(12) United States Patent
Naughton et al.

(10) Patent No.: US 10,675,303 B2
(45) Date of Patent: *Jun. 9, 2020

(54) EXTRACELLULAR MATRIX COMPOSITIONS FOR THE TREATMENT OF CANCER

(71) Applicant: ADAPTIVE BIOLOGIX, INC., San Diego, CA (US)

(72) Inventors: Gail K. Naughton, Encinitas, CA (US); Emmett Pinney, Poway, CA (US)

(73) Assignee: Adaptive Biologix, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/206,816

(22) Filed: Nov. 30, 2018

(65) Prior Publication Data
US 2019/0201439 A1 Jul. 4, 2019

Related U.S. Application Data

(63) Continuation of application No. 15/362,261, filed on Nov. 28, 2016, now Pat. No. 10,143,708, which is a continuation of application No. 14/711,646, filed on May 13, 2015, now Pat. No. 9,506,038, which is a continuation of application No. 12/822,126, filed on Jun. 23, 2010, now Pat. No. 9,034,312, which is a continuation-in-part of application No. 12/363,479, filed on Jan. 30, 2009, now Pat. No. 8,852,637.

(60) Provisional application No. 61/114,966, filed on Nov. 14, 2008.

(51) Int. Cl.
| | |
|---|---|
| *A61K 35/00* | (2006.01) |
| *A61K 35/12* | (2015.01) |
| *C12N 5/09* | (2010.01) |
| *A61K 35/13* | (2015.01) |
| *A61P 35/00* | (2006.01) |
| *A61K 33/24* | (2019.01) |
| *A61K 35/33* | (2015.01) |
| *A61K 35/54* | (2015.01) |
| *A61K 45/06* | (2006.01) |

(52) U.S. Cl.
CPC .............. *A61K 35/12* (2013.01); *A61K 33/24* (2013.01); *A61K 35/13* (2013.01); *A61K 35/33* (2013.01); *A61K 35/54* (2013.01); *A61K 45/06* (2013.01); *A61P 35/00* (2018.01); *C12N 5/0693* (2013.01)

(58) Field of Classification Search
CPC ............................. A61K 35/12; C12N 5/0693
See application file for complete search history.

(56) References Cited

U.S. PATENT DOCUMENTS

| | | | |
|---|---|---|---|
| 5,980,046 | A | 11/1999 | Naughton et al. |
| 5,980,946 | A | 11/1999 | Jones et al. |
| 2007/0077232 | A1 | 4/2007 | Naughton et al. |
| 2008/0220466 | A1 | 9/2008 | Fulga et al. |
| 2008/0254145 | A1 | 10/2008 | Colin et al. |

FOREIGN PATENT DOCUMENTS

| | | |
|---|---|---|
| IL | 138723 A | 11/2005 |
| JP | A 2002-530069 | 5/2000 |
| JP | 2006-249031 A | 9/2006 |
| RU | 2311892 C2 | 12/2007 |
| WO | WO 1990/002796 A1 | 3/1990 |
| WO | WO 1995/030423 | 11/1995 |
| WO | WO 1995/1033821 A | 12/1995 |
| WO | WO 1996/039101 A1 | 12/1996 |
| WO | WO 2006/026652 A2 | 3/2006 |
| WO | A 2007-528252 | 5/2006 |
| WO | WO 2006/055981 A2 | 5/2006 |
| WO | WO 2006/067633 A2 | 6/2006 |
| WO | WO 2003/073998 A2 | 9/2006 |

OTHER PUBLICATIONS

Alberts et al.: "*Cancer as a Microevolutionary Process*"; Molecular Biology of the Cell, 4th edition,.New York, Garland Science, 2002. Figure 23-15, paue 1 of 1.
Azimzadeh et al.: "*Xenograft rejection: molecular mechanisms and therapeutic prospects*"; Hematology and Cell Therapy 38(4):331-343, 1997.
Barker C.R. et al.: *The topoisomerase II-Hsp90 complex: a new chemotherapeutic target*?; Int J Cancer, Jun. 1, 2006, 118(11): p. 2685-2693 (Abstract).
Chemical Encyclopedia, vol. 2, Editorship Soviet Encyclopedia, M, 1990, pp. 432-433 (English Translation).
Falanga et al.: "*Low Oxygen Stimulates Proliferation of Fibroblasts Seeded as Single Cells*"; J. Cell. Physiol., 1993, vol. 154, p. 506-510.
Falanga et al.: "*Low Oxygen Tension Stimulates Collagen Synthesis and COL1A1 Transcription Through the Action of TGF-β1*"; J. Cell. Physiol., 2002, vol. 191, p. 42-50.
Gould et al.: "*Direct and indirect recognition: the role of MHC antigens in graft rejection*"; Immunology Today, 20(2):77-82, Feb. 1999.
International Search Report dated May 20, 2010, regarding PCT/US2010/056378.
Indian Examination Report dated Jul. 21, 2017 regarding 3769/CHENP/2011.
International Search Report (ISR) dated Mar. 20, 2009 Re PCT/US2009/032677.

(Continued)

*Primary Examiner* — Marcia S Noble
(74) *Attorney, Agent, or Firm* — DLA Piper LLP (US)

(57) ABSTRACT

The present invention is directed to methods of inhibiting cancer cell growth or proliferation by contacting the cancer cell with an extracellular matrix (ECM) composition. Also provided are methods of delivering a chemotherapeutic agent to a cancer cell by contacting a cancer cell with an extracellular matrix composition containing a chemotherapeutic agent. Also provided are compositions containing ECM and a chemotherapeutic agent.

15 Claims, 18 Drawing Sheets

(56) References Cited

OTHER PUBLICATIONS

Keira et al.: "*Experimental model for fibroblast culture*"; Act Cir Bras 19:11-16, 2004; url: http://www.scielo.br/acb.
Lu et al.: '*Different spontaneous pulmonary metastasis inhibitions against iewis lung carcinoma in mice by bisdioxcuiuerazine compounds of different treatment schedules*; Sci Pharrn., 78(11:13-20 (2010).
Moiseenko, MD VM: "*Modern tactics treatment of patients with malignant neoplasms of bone metastases*"; (Manual for physicians); Oncology Institute, Petrova RU, Dec. 21, 2012, 8 pages; (translation).
Pavelic et al.: "*Growth of Human Urological Tumors on Extracellular Matrix as a Model for the in Vitro Cultivation of Primary Human Tumor Explants*"; Cancer Res 46:3653-3662, Jul. 1, 1986.

Cells are uniform

MDA435 Cells

Single dose

EXTRACELLULAR MATRIX COMPOSITIONS FOR THE TREATMENT OF CANCER

CROSS-REFERENCE TO RELATED APPLICATIONS

This application is a continuation application of U.S. application Ser. No. 15/362,261 filed Nov. 28, 2016, now pending; which is a continuation application of U.S. application Ser. No. 14/711,646 filed May 13, 2015, now issued as U.S. Pat. No. 9,506,038; which is a continuation application of U.S. application Ser. No. 12/822,126 filed Jun. 23, 2010, now issued as U.S. Pat. No. 9,034,312; which is a continuation-in-part application of U.S. application Ser. No. 12/363,479 filed Jan. 30, 2009, now issued as U.S. Pat. No. 8,852,637, which claims the benefit under 35 U.S.C. § 119(e) to U.S. Application Ser. No. 61/114,966 filed Nov. 14, 2008. The disclosure of each of the prior applications is considered part of and is incorporated by reference in the disclosure of this application.

BACKGROUND OF THE INVENTION

Field of the Invention

The present invention relates generally to use of extracellular matrix compositions and more specifically, the use of extracellular matrix compositions to inhibit cell proliferation.

Background Information

The extracellular matrix (ECM) is a complex structural entity surrounding and supporting cells that are found in vivo within mammalian tissues. The ECM is often referred to as the connective tissue. The ECM is primarily composed of three major classes of biomolecules including structural proteins such as collagens and elastins, specialized proteins such as fibrillins, fibronectins, and laminins, and proteoglycans.

Growth of ECM compositions in vitro and their use in a variety of therapeutic and medical applications have been described in the art. One therapeutic application of such ECM compositions includes treatment and repair of soft tissue and skin defects such as wrinkles and scars.

The repair or augmentation of soft tissue defects caused by defects, such as, acne, surgical scarring or aging has proven to be very difficult. A number of materials have been used to correct soft tissue defects with varying degrees of success, however, no material has been completely safe and effective. For example, silicon causes a variety of physiological and clinical problems including long term side effects, such as nodules, recurring cellulitis and skin ulcers.

Collagen compositions have also been used as an injectable material for soft tissue augmentation. Collagen is the main protein of connective tissue and the most abundant protein in mammals, making up about 25% of the total protein content. There are currently 28 types of collagen described in literature (see, e.g., Tables 1 and 2 infra, for a detailed listing). However, over 90% of the collagen in the body are Collagens I, II, III, and IV.

Different collagen materials have been used for treatment of soft tissue defects, such as reconstituted injectable bovine collagen, crosslinked collagen, or other xenogeneic collagens. However, several problems exist with such collagens. A common problem includes the complexity and high cost of producing the implant materials to remove potentially immunogenic substances to avoid allergic reactions in the subject. Additionally, treatments using such collagens have not proven long lasting.

Other materials have also been described that may be used for soft tissue repair or augmentation, such as, biocompatible ceramic particles in aqueous gels (U.S. Pat. No. 5,204,382), thermoplastic and/or thermosetting materials (U.S. Pat. No. 5,278,202), and lactic acid based polymer blends (U.S. Pat. No. 4,235,312). Additionally, use of naturally secreted extracellular matrix compositions have also been described (U.S. Pat. No. 6,284,284). However, such materials have all proven to have limitations.

Accordingly, new materials are needed for soft tissue repair and augmentation that overcome the deficiencies of prior materials. The need exists to provide a safe, injectable, long lasting, bioabsorbable, soft tissue repair and augmentation material.

In vitro cultured ECM compositions can additionally be used to treat damaged tissue, such as, damaged cardiac muscle and related tissue. The compositions are useful as implants or biological coatings on implantable devices, such as, stents or vascular prosthesis to promote vascularization in organs, such as the heart and related tissue.

Coronary heart disease (CHD), also called coronary artery disease (CAD), ischaemic heart disease, and atherosclerotic heart disease, is characterized by a narrowing of the small blood vessels that supply blood and oxygen to the heart. Coronary heart disease is usually caused by a condition called atherosclerosis, which occurs when fatty material and plaque builds up on the walls of arteries causing the arteries to narrow. As the coronary arteries narrow, blood flow to the heart can slow down or stop, causing chest pain (stable angina), shortness of breath, heart attack, and other symptoms.

Coronary heart disease (CHD) is the leading cause of death in the United States for men and women. According to the American Heart Association, more than 15 million people have some form of the condition. While the symptoms and signs of coronary heart disease are evident in the advanced state of the disease, most individuals with coronary heart disease show no evidence of disease for decades as the disease progresses before a sudden heart attack occurs. The disease is the most common cause of sudden death, and is also the most common reason for death of men and women over 20 years of age. According to present trends in the United States, half of healthy 40-year-old males will develop CHD in the future, as well as one in three healthy 40-year-old women.

Current methods for improving blood flow in a diseased or otherwise damaged heart involve invasive surgical techniques, such as, coronary by-pass surgery, angioplasty, and endarterectomy. Such procedures naturally involve high-degrees of inherent risk during and after surgery, and often only provide a temporary remedy to cardiac ischemia. Accordingly, new treatment options are required to increase the success of currently available techniques for treating CHD and related symptoms.

In vitro cultured ECM compositions can additionally be used to repair and/or regenerate damaged cells or tissue, such as chondral or osteochondral cells. Osteochondral tissue is any tissue that relates to or contains bone or cartilage. The compositions of the present invention are useful for treatment of osteochondral defects, such as degenerative connective tissue diseases, such as rheumatoid and/or osteoarthritis as well as defects in patients who have cartilage defects due to trauma.

Current attempts at repairing osteochondral defects include implantation of human chondrocytes in biocompatible and biodegradable hydrogel grafts in attempts to improve the possibilities to restore articular cartilage lesions. Additionally, the technique of chondrocyte culture in alginate beads or a matrix including polysulphated alginate has been described to generate a hyaline-like cartilaginous tissue. However, attempts at repairing endochondral lesions of articular cartilage by implantation of human autologous chondrocytes have had limited success. Accordingly, new treatment options are required to increase the success of currently available techniques for treating osteochondral defects.

In vitro cultured ECM compositions are also useful in tissue culture systems for generation of engineered tissue implants. The field of tissue engineering involves the use of cell culture technology to generate new biological tissues or repair damaged tissues. Fueled in part, by the stem cell revolution, tissue engineering technology offers the promise of tissue regeneration and replacement following trauma or treatment of degenerative diseases. It can also be used in the context of cosmetic procedures.

Tissue engineering techniques can be used to generate both autologous and heterologous tissue or cells using a variety of cell types and culture techniques. In creating an autologous implant, donor tissue may be harvested and dissociated into individual cells, and subsequently attached and cultured on a substrate to be implanted at the desired site of the functioning tissue. Many isolated cell types can be expanded in vitro using cell culture techniques, however, anchorage dependent cells require specific environments, often including the presence of a three-dimensional scaffold, to act as a template for growth.

Current tissue engineering technology provide generally, artificial implants. Successful cell transplantation therapy depends on the development of suitable substrates for both in vitro and in vivo tissue culture. Thus the development of an extracellular matrix that contains only natural materials and that is suitable for implantation would have more of the characteristics of the endogenous tissue. Accordingly, generation of natural extracellular matrix material is an ongoing challenge in the field of tissue engineering.

SUMMARY OF THE INVENTION

The present invention is based in part on the discovery that extracellular matrix (ECM) compositions can inhibit the growth of cancer cells in vivo. Accordingly, in one embodiment of the present invention, there are provided methods of inhibiting cancer cell growth or proliferation, by contacting the cancer cell with an extracellular matrix composition as described herein.

In another embodiment of the present invention, there are provided methods of delivering a chemotherapeutic agent to a cell or tissue, including contacting the cell or tissue with an extracellular matrix composition containing a chemotherapeutic agent.

In still another embodiment of the present invention there are provided compositions containing ECM and a chemotherapeutic agent. In some embodiments, the composition further contains an immunomodulatory agent.

In yet another embodiment of the present invention there are provided methods of inhibiting metastasis of a cancer cell by contacting the cancer cell with an extracellular matrix composition as described herein. In various embodiments, the cancer cell is metastatic, for example, the cancer cell may be from a metastatic tumor, such as a metastatic primary tumor.

DETAILED DESCRIPTION OF THE INVENTION

Figure 1:
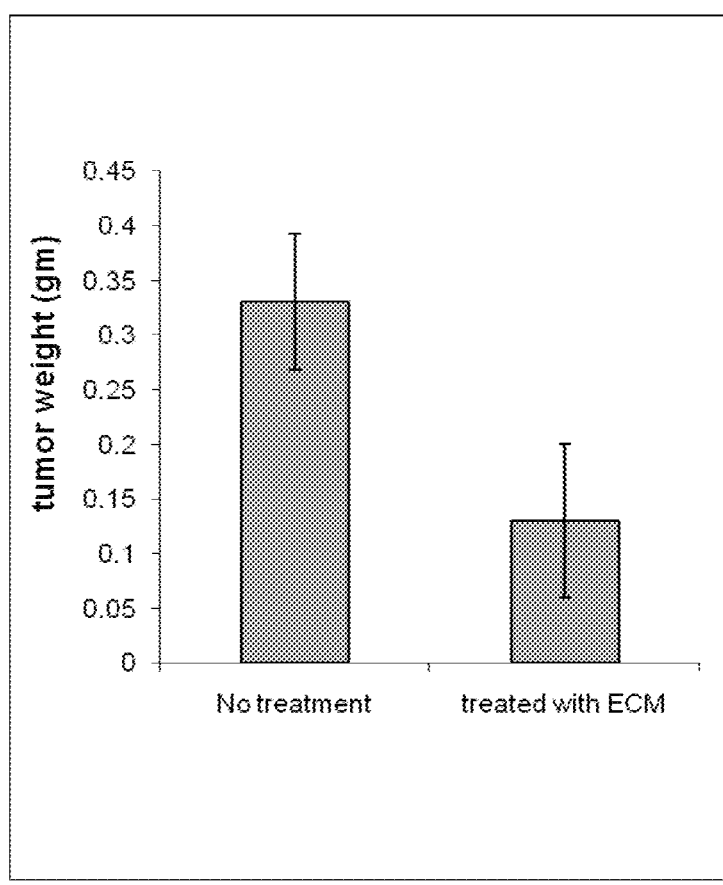
FIG. 1 shows a plot of tumor weight of B16 cells in the presence and absence of ECM in the CAM assay.

The present invention relates to methods of using extracellular matrix compositions for the inhibition of growth or proliferation of cancer cells alone or as a biological vehicle for the delivery of a chemotherapeutic agent.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

In one embodiment of the present invention, there are provided methods of inhibiting cancer cell growth or proliferation, in which the method includes contacting the cancer cell with an extracellular matrix composition. In some embodiments, the cancer cell is metastatic. In some embodiments, the ECM may be a soluble fraction, and in other embodiments the ECM may be a non-soluble fraction. In still other embodiments, the ECM may be a combination of soluble and non-soluble fractions.

In certain embodiments, the cancer cell is from a tumor, such as a primary or secondary tumor. In certain embodiments, the tumor is metastatic. In some aspects, the cancer is selected from the group consisting of melanoma, glioma, and adenocarcinoma. In other aspects the cancer is a cancer of the adrenal gland, bladder, bone, bone marrow, brain, spine, breast, cervix, gall bladder, ganglia, gastrointestinal tract, stomach, colon, heart, kidney, liver, lung, muscle, ovary, pancreas, parathyroid, penis, prostate, salivary glands, skin, spleen, testis, thymus, thyroid, or uterus. In one aspect the cancer is breast cancer; in another aspect the cancer is melanoma; and in another aspect the cancer is colon cancer.

In another embodiment of the present invention, there are provided methods of delivering a chemotherapeutic agent to a cancer cell, wherein the method includes contacting a cancer cell with an extracellular matrix composition containing a chemotherapeutic agent.

In one aspect, the contacting is in the surgical margin of the area from which a tumor has been excised. In such embodiments, a tumor is removed from a subject using standard surgical techniques known to the clinician. ECM compositions of the invention may be placed in the space left upon excision of the tumor (resection), so that the ECM is in contact with the surgical margin. In certain embodiments, the ECM may inhibit the growth of cancer cells residing in the tumor margin. In some embodiments, the ECM composition may further contain a chemotherapeutic agent with or without an immunomodulatory agent. The use of the invention ECM compositions in treatment of cancer following surgical resection has the advantage of delivering localized and sustained-release delivery of a chemotherapeutic and/or immunomodulatory agent to the tumor site. Additional benefits can include improved healing of surgical wounds and improved cosmetic outcome.

In still another embodiment of the present invention there are provided compositions containing ECM and a chemotherapeutic agent. In some embodiments, the composition further contains an immunomodulatory agent.

In some embodiments the extracellular matrix compositions are generated by culturing cells under hypoxic conditions on a two- or three-dimensional surface in a suitable growth medium. The culturing method produces both soluble and non-soluble fractions which may be used separately or in combination to obtain physiologically acceptable compositions having a variety of applications. In other embodiments, the cells may be cultured under standard or normal oxygen conditions.

The compositions of the present invention have a variety of applications including, but not limited to, inhibiting growth or proliferation of cancer cells, delivery of therapeutic agents, promoting repair and/or regeneration of damaged cells or tissues, use in patches to promote tissue regeneration, use in tissue culture systems for culturing cells, such as stem cells, use in surface coatings used in association with implantable devices (e.g., pacemakers, stents, stent grafts, vascular prostheses, heart valves, shunts, drug delivery ports or catheters), promoting soft tissue repair, augmentation, and/or improvement of a skin surface, such as wrinkles, use as a biological anti-adhesion agent or as a biological vehicle for cell delivery or maintenance at a site of delivery.

The invention is based in part, on the discovery that cells cultured on two- or three-dimensional surfaces under conditions that stimulate the early embryonic environment (hypoxia and reduced gravitational forces) prior to angiogenesis produces extracellular matrix compositions with fetal properties, including generation of embryonic proteins. Growth of cells under hypoxic conditions demonstrate a unique ECM with fetal properties and growth factor expression. Unlike the culturing of ECM under traditional culture conditions, over 5000 genes are differentially expressed in ECM cultured under hypoxic conditions. This results in a cultured ECM that has different properties and a different biological composition. For example, an ECM produced under hypoxic conditions is similar to fetal mesenchymal tissue in that it is relatively rich in collagens type III, IV, and V, and glycoproteins such as fibronectin, SPARC, thrombospondin, and hyaluronic acid.

Hypoxia also enhances expression of factors which regulate wound healing and organogenesis, such as VEGF, FGF-7, and TGF-β, as well as multiple Wnt factors including Wnt's 2b, 4, 7a, 10a, and 11. Cultured embryonic human ECM also stimulates an increase of metabolic activity in human fibroblasts in vitro, as measured by increased enzymatic activity. Additionally, there is an increase in cell number in response to the cultured embryonic ECM.

In various embodiments, the present invention involves methods for making extracellular matrix compositions that include one or more embryonic proteins and applications thereof. In particular the compositions are generated by culturing cells under hypoxic conditions on a two- or three-dimensional surface in a suitable growth medium. The compositions are derived by growing cells on a framework resulting in a multi-layer cell culture system. Cells grown on a framework support, in accordance with the present invention, grow in multiple layers, forming a cellular matrix. Growth of the cultured cells under hypoxic conditions results in differential gene expression as the result of hypoxic culturing conditions versus traditional culture.

Extracellular matrix (ECM) is a composition of proteins and biopolymers that substantially comprise tissue that is produced by cultivation of cells. Stromal cells, such as fibroblasts, are an anchorage dependant cell type requiring growth while attached to materials and surfaces suitable for cell culture. The ECM materials produced by the cultured cells are deposited in a three-dimensional arrangement providing spaces for the formation of tissue-like structures.

The cultivation materials providing three-dimensional architectures are referred to as scaffolds. Spaces for deposition of ECM are in the form of openings within, for example woven mesh or interstitial spaces created in a compacted configuration of spherical beads, called microcarriers.

As used herein, "extracellular matrix composition" includes both soluble and non-soluble fractions or any portion or combination thereof. The non-soluble fraction includes those secreted extracellular matrix proteins and biological components that are deposited on the support or scaffold. The soluble fraction refers to culture media in which cells have been cultured and into which the cells have secreted active agent(s) and includes those proteins and biological components not deposited on the scaffold. Both fractions may be collected, and optionally further processed, and used individually or in combination in a variety of applications as described herein. ECM may also be obtained from cadaver tissues (U.S. Pat. Nos. 6,284,284 and 6,372,494).

The soluble fraction may be concentrated or diluted to achieve an optimal concentration. In certain embodiments, the concentration may be about 1 mg/mL, about 5 mg/mL, about 10 mg/mL, about 50 mg/mL, about 100 mg/mL, or about 200 mg/mL. The concentration may be in a range of about 0.1 mg/mL to 1000 mg/mL, or about 1 to 200 mg/mL, or about 10 mg/mL to 100 mg/mL.

The soluble fraction may be further fractionated according to molecular weight (e.g., by dialysis, filtration, or chromatography) so that the majority of the solute molecules in fraction meet a particular molecular weight cutoff. It will be recognized that the cutoff values are not absolute but that a majority (e.g., 70%, 80%, 90%, or 95%) of the solute molecules contained in a given fraction meet the molecular weight cutoff. Accordingly, in certain embodiments of the methods provided herein, the ECM composition may include a soluble fraction in which 70%, or 80%, or 90% of the solute molecules contained therein have a molecular weight of less than 5,000 Daltons, or less than 10,000 Daltons, or less than 30,000 Daltons, or less than 100,000 Daltons. In other embodiments, the ECM may include a soluble fraction in which the solute molecules contained therein have a molecular weight of greater than 5,000 Daltons, or greater than 10,000 Daltons, or greater than 30,000 Daltons, or greater than 100,000 Daltons. In other embodiments, the ECM may include a soluble fraction in which the solute molecules contained therein have a molecular weight between 10,000 and 100,000 Daltons, or 30,000 to 100,000 Daltons, or 10,000 to 30,000 Daltons.

The two- or three-dimensional support or scaffold used to culture stromal cells may be of any material and/or shape that: (a) allows cells to attach to it (or can be modified to allow cells to attach to it); and (b) allows cells to grow in more than one layer (i.e., form a three dimensional tissue). In other embodiments, a substantially two-dimensional sheet or membrane may be used to culture cells that are sufficiently three dimensional in form.

The biocompatible material is formed into a two- or three-dimensional structure or scaffold, where the structure has interstitial spaces for attachment and growth of cells into a three dimensional tissue. The openings and/or interstitial spaces of the framework in some embodiments are of an appropriate size to allow the cells to stretch across the openings or spaces. Maintaining actively growing cells stretched across the framework appears to enhance production of the repertoire of growth factors responsible for the activities described herein. If the openings are too small, the cells may rapidly achieve confluence but be unable to easily exit from the mesh. These trapped cells may exhibit contact inhibition and cease production of the appropriate factors necessary to support proliferation and maintain long term cultures. If the openings are too large, the cells may be unable to stretch across the opening, which may lead to a decrease in stromal cell production of the appropriate factors necessary to support proliferation and maintain long term cultures. Typically, the interstitial spaces are at least about 100 um, at least 140 um, at least about 150 um, at least about 180 um, at least about 200 um, or at least about 220 um. When using a mesh type of matrix, as exemplified herein, we have found that openings ranging from about 100 µm to about 220 µm will work satisfactorily. However, depending upon the three-dimensional structure and intricacy of the framework, other sizes are permissible. Any shape or structure that allows the cells to stretch and continue to replicate and grow for lengthy time periods may function to elaborate the cellular factors in accordance with the methods herein.

In some aspects, the three dimensional framework is formed from polymers or threads that are braided, woven, knitted or otherwise arranged to form a framework, such as a mesh or fabric. The materials may also be formed by casting of the material or fabrication into a foam, matrix, or sponge-like scaffold. In other aspects, the three dimensional framework is in the form of matted fibers made by pressing polymers or other fibers together to generate a material with interstitial spaces. The three dimensional framework may take any form or geometry for the growth of cells in culture. Thus, other forms of the framework, as further described below, may suffice for generating the appropriate conditioned medium.

A number of different materials may be used to form the scaffold or framework. These materials include non-polymeric and polymeric materials. Polymers, when used, may be any type of polymer, such as homopolymers, random polymers, copolymers, block polymers, coblock polymers (e.g., di, tri, etc.), linear or branched polymers, and cross-linked or non-crosslinked polymers. Non-limiting examples of materials for use as scaffolds or frameworks include, among others, glass fibers, polyethylenes, polypropylenes, polyamides (e.g., nylon), polyesters (e.g., dacron), polystyrenes, polyacrylates, polyvinyl compounds (e.g., polyvinylchloride; PVC), polycarbonates, polytetrafluorethylenes (PTFE; TEFLON), thermanox (TPX), nitrocellulose, polysaccharides (e.g., celluloses, chitosan, agarose), polypeptides (e.g., silk, gelatin, collagen), polyglycolic acid (PGA), and dextran.

In some aspects, the framework may be made of materials that degrade over time under the conditions of use. Biodegradable also refers to absorbability or degradation of a compound or composition when administered in vivo or under in vitro conditions. Biodegradation may occur through the action of biological agents, either directly or indirectly. Non-limiting examples of biodegradable materials include, among others, polylactide, polyglycolide, poly(trimethylene carbonate), poly(lactide-co-glycolide) (i.e., PLGA), polyethylene terephtalate (PET), polycaprolactone, catgut suture material, collagen (e.g., equine collagen foam), polylactic acid, or hyaluronic acid. For example, these materials may be woven into a three-dimensional framework such as a collagen sponge or collagen gel.

In other aspects, where the cultures are to be maintained for long periods of time, cryopreserved, and/or where additional structural integrity is desired, the three dimensional framework may be comprised of a nonbiodegradable material. As used herein, a nonbiodegradable material refers to a material that does not degrade or decompose significantly under the conditions in the culture medium. Exemplary nondegradable materials include, as non-limiting examples, nylon, dacron, polystyrene, polyacrylates, polyvinyls, polytetrafluoroethylenes (PTFE), expanded PTFE (ePTFE), and cellulose. An exemplary nondegrading three dimensional framework comprises a nylon mesh, available under the tradename Nitex®, a nylon filtration mesh having an average pore size of 140 µm and an average nylon fiber diameter of 90 µm (#3-210/36, Tetko, Inc., N.Y.).

In other aspects, the scaffold or framework is a combination of biodegradable and non-biodegradable materials. The non-biodegradable material provides stability to the scaffold during culturing while the biodegradable material allows formation of interstitial spaces sufficient for generating cell networks that produce the cellular factors sufficient for therapeutic applications. The biodegradable material may be coated onto the non-biodegradable material or woven, braided or formed into a mesh. Various combinations of biodegradable and non-biodegradable materials may be used. An exemplary combination is poly(ethylene therephtalate) (PET) fabrics coated with a thin biodegradable polymer film, poly[D-L-lactic-co-glycolic acid), in order to obtain a polar structure.

In various aspects, the scaffold or framework material may be pre-treated prior to inoculation with cells to enhance cell attachment. For example, prior to inoculation with cells, nylon screens in some embodiments are treated with 0.1 M acetic acid, and incubated in polylysine, fetal bovine serum, and/or collagen to coat the nylon. Polystyrene could be similarly treated using sulfuric acid. In other embodiments, the growth of cells in the presence of the three-dimensional support framework may be further enhanced by adding to the framework or coating it with proteins (e.g., collagens, elastin fibers, reticular fibers), glycoproteins, glycosaminoglycans (e.g., heparan sulfate, chondroitin-4-sulfate, chondroitin-6-sulfate, dermatan sulfate, keratan sulfate, etc.), fibronectins, and/or glycopolymer (poly[N-p-vinylbenzyl-D-lactoamide], PVLA) in order to improve cell attachment. Treatment of the scaffold or framework is useful where the material is a poor substrate for the attachment of cells.

In one aspect, mesh is used for production of ECM. The mesh is a woven nylon 6 material in a plain weave form with approximately 100 µm openings and approximately 125 µm thick. In culture, fibroblast cells attach to the nylon through charged protein interactions and grow into the voids of the mesh while producing and depositing ECM proteins. Mesh openings that are excessively large or small may not be effective but could differ from those above without substantially altering the ability to produce or deposit ECM. In another aspect, other woven materials are used for ECM production, such as polyolefin's, in weave configurations giving adequate geometry for cell growth and ECM deposition.

For example, nylon mesh is prepared for cultivation in any of the steps of the invention by cutting to the desired size, washing with 0.1-0.5M acetic acid followed by rinsing with high purity water and then steam sterilized. For use as a three-dimensional scaffold for ECM production the mesh is sized into squares approximately 10 cm×10 cm. However, the mesh could be any size appropriate to the intended application and may be used in any of the methods of the present invention, including cultivation methods for inoculation, cell growth and ECM production and preparation of the final form.

In other aspects, the scaffold or framework for generating the cultured three dimensional tissues is composed of microcarriers, which are beads or particles. The beads may be microscopic or macroscopic and may further be dimensioned so as to permit penetration into tissues or compacted to form a particular geometry. In some tissue penetrating embodiments, the framework for the cell cultures comprises particles that, in combination with the cells, form a three dimensional tissue. The cells attach to the particles and to each other to form a three dimensional tissue. The complex of the particles and cells is of sufficient size to be administered into tissues or organs, such as by injection or catheter.

As used herein, a "microcarrier" refers to a particle having size of nanometers to micrometers, where the particles may be any shape or geometry, being irregular, non-spherical, spherical, or ellipsoid. Typically growth on beads or microcarriers is referred to as a two-dimensional system or scaffold or framework.

The size of the microcarriers suitable for the purposes herein can be of any size suitable for the particular application. In some embodiments, the size of microcarriers suitable for the three dimensional tissues may be those administrable by injection. In some embodiments, the microcarriers have a particle size range of at least about 1 µm, at least about 10 µm, at least about 25 µm, at least about 50 µm, at least about 100 µm, at least about 200 µm, at least about 300 µm, at least about 400 µm, at least about 500 µm, at least about 600 µm, at least about 700 µm, at least about 800 µm, at least about 900 µm, at least about 1000 µm.

In some aspects in which the microcarriers are made of biodegradable materials. In some aspects, microcarriers comprising two or more layers of different biodegradable polymers may be used. In some embodiments, at least an outer first layer has biodegradable properties for forming the three dimensional tissues in culture, while at least a biodegradable inner second layer, with properties different from the first layer, is made to erode when administered into a tissue or organ.

In some aspects, the microcarriers are porous microcarriers. Porous microcarriers refer to microcarriers having interstices through which molecules may diffuse in or out from the microparticle. In other embodiments, the microcarriers are nonporous microcarriers. A nonporous microparticle refers to a microparticle in which molecules of a select size do not diffuse in or out of the microparticle.

Microcarriers for use in the compositions are biocompatible and have low or no toxicity to cells. Suitable microcarriers may be chosen depending on the tissue to be treated, type of damage to be treated, the length of treatment desired, longevity of the cell culture in vivo, and time required to form the three dimensional tissues. The microcarriers may comprise various polymers, natural or synthetic, charged (i.e., anionic or cationic) or uncharged, biodegradable, or non-biodegradable. The polymers may be homopolymers, random copolymers, block copolymers, graft copolymers, and branched polymers.

In some aspects, the microcarriers comprise non-biodegradable microcarriers. Non-biodegradable microcapsules and microcarriers include, but not limited to, those made of polysulfones, poly(acrylonitrile-co-vinyl chloride), ethylene-vinyl acetate, hydroxyethylmethacrylate-methyl-methacrylate copolymers. These are useful to provide tissue bulking properties or in embodiments where the microcarriers are eliminated by the body.

In some aspects, the microcarriers comprise degradable scaffolds. These include microcarriers made from naturally occurring polymers, non-limiting example of which include, among others, fibrin, casein, serum albumin, collagen, gelatin, lecithin, chitosan, alginate or poly-amino acids such as poly-lysine. In other aspects, the degradable microcarriers are made of synthetic polymers, non-limiting examples of which include, among others, polylactide (PLA), polyglycolide (PGA), poly(lactide-co-glycolide) (PLGA), poly (caprolactone), polydioxanone trimethylene carbonate, polyhybroxyalkonates (e.g., poly(hydroxybutyrate), poly (ethyl glutamate), poly(DTH iminocarbony(bisphenol A iminocarbonate), poly(ortho ester), and polycyanoacrylates.

In some aspects, the microcarriers comprise hydrogels, which are typically hydrophilic polymer networks filled with water. Hydrogels have the advantage of selective trigger of polymer swelling. Depending on the composition of the polymer network, swelling of the microparticle may be triggered by a variety of stimuli, including pH, ionic strength, thermal, electrical, ultrasound, and enzyme activities. Non-limiting examples of polymers useful in hydrogel compositions include, among others, those formed from polymers of poly(lactide-co-glycolide); poly(N-isopropylacrylamide); poly(methacrylic acid-g-polyethylene glycol); polyacrylic acid and poly(oxypropylene-co-oxyethylene) glycol; and natural compounds such as chrondroitan sulfate, chitosan, gelatin, fibrinogen, or mixtures of synthetic and natural polymers, for example chitosan-poly (ethylene oxide). The polymers may be crosslinked reversibly or irreversibly to form gels adaptable for forming three dimensional tissues.

In accordance with the present invention the culturing method is applicable to proliferation of different types of cells, including stromal cells, such as fibroblasts, and particularly primary human neonatal foreskin fibroblasts. In various aspects, the cells inoculated onto the framework can be stromal cells comprising fibroblasts, with or without other cells, as further described below. In some embodiments, the cells are stromal cells that are typically derived from connective tissue, including, but not limited to: (1) bone; (2) loose connective tissue, including collagen and elastin; (3) the fibrous connective tissue that forms ligaments and tendons, (4) cartilage; (5) the extracellular matrix of blood; (6) adipose tissue, which comprises adipocytes; and (7) fibroblasts.

Stromal cells can be derived from various tissues or organs, such as skin, heart, blood vessels, bone marrow, skeletal muscle, liver, pancreas, brain, foreskin, which can be obtained by biopsy (where appropriate) or upon autopsy. In one aspect, fetal fibroblasts can be obtained in high quantity from foreskin, such as neonatal foreskins.

In some aspects, the cells comprise fibroblasts, which can be from a fetal, neonatal, adult origin, or a combination thereof. In some aspects, the stromal cells comprise fetal fibroblasts, which can support the growth of a variety of different cells and/or tissues. As used herein, a fetal fibroblast refers to fibroblasts derived from fetal sources. As used herein, neonatal fibroblast refers to fibroblasts derived from newborn sources. Under appropriate conditions, fibroblasts can give rise to other cells, such as bone cells, fat cells, and smooth muscle cells and other cells of mesodermal origin. In some embodiments, the fibroblasts comprise dermal fibroblasts, which are fibroblasts derived from skin. Normal human dermal fibroblasts can be isolated from neonatal foreskin. These cells are typically cryopreserved at the end of the primary culture.

In other aspects, the three-dimensional tissue can be made using stem or progenitor cells, either alone, or in combination with any of the cell types discussed herein. Stem and progenitor cells include, by way of example and not limitation, embryonic stem cells, hematopoietic stem cells, neuronal stem cells, epidermal stem cells, and mesenchymal stem cells.

In some embodiments, a "specific" three-dimensional tissue can be prepared by inoculating the scaffold with cells derived from a particular organ, i.e., skin, heart, and/or from a particular individual who is later to receive the cells and/or tissues grown in culture in accordance with the methods described herein.

For certain uses in vivo it is preferable to obtain the stromal cells from the patient's own tissues. The growth of cells in the presence of the stromal support framework can be further enhanced by adding to the framework, or coating the framework support with proteins, e.g., collagens, laminins, elastic fibers, reticular fibers, glycoproteins; glycosaminoglycans, e.g., heparan sulfate, chondroitin-4-sulfate, chondroitin-6-sulfate, dermatan sulfate, keratan sulfate, etc.; a cellular matrix, and/or other materials.

Thus, since the two- or three-dimensional culture system described herein is suitable for growth of diverse cell types and tissues, and depending upon the tissue to be cultured and the collagen types desired, the appropriate stromal cells may be selected to inoculate the framework.

While the methods and applications of the present invention are suitable for use with different cell types, such as tissue specific cells or different types of stromal cells as discussed herein, derivation of the cells for use with the present invention may also be species specific. Accordingly, ECM compositions may be generated that are species specific. For example, the cells for use in the present invention may include human cells. For example, the cells may be human fibroblasts. Likewise, the cells are from another species of animal, such as equine (horse), canine (dog) or feline (cat) cells. Additionally, cells from one species or strain of species may be used to generate ECM compositions for use in other species or related strains (e.g., allogeneic, syngeneic and xenogeneic). It is also to be appreciated that cells derived from various species may be combined to generate multi-species ECM compositions.

Accordingly, the methods and compositions of the present invention are suitable in applications involving non-human animals. As used herein, "veterinary" refers to the medical science concerned or connected with the medical or surgical treatment of animals, especially domestic animals. Common veterinary animals may include mammals, amphibians, avians, reptiles and fishes. For example, typical mammals may include dogs, cats, horses, rabbits, primates, rodents, and farm animals, such as cows, horses, goats, sheep, and pigs.

As discussed above, additional cells may be present in the culture with the stromal cells. These additional cells may have a number of beneficial effects, including, among others, supporting long term growth in culture, enhancing synthesis of growth factors, and promoting attachment of cells to the scaffold. Additional cell types include as non-limiting examples, smooth muscle cells, cardiac muscle cells, endothelial cells, skeletal muscle cells, endothelial cells, pericytes, macrophages, monocytes, and adipocytes. Such cells may be inoculated onto the framework along with fibroblasts, or in some aspects, in the absence of fibroblasts. These stromal cells may be derived from appropriate tissues or organs, including, by way of example and not limitation, skin, heart, blood vessels, bone marrow, skeletal muscle, liver, pancreas, and brain. In other aspects, one or more other cell types, excluding fibroblasts, are inoculated onto the scaffold. In still other aspects, the scaffolds are inoculated only with fibroblast cells.

Fibroblasts may be readily isolated by disaggregating an appropriate organ or tissue which is to serve as the source of the fibroblasts. For example, the tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include but are not limited to trypsin, chymotrypsin, collagenase, elastase, hyaluronidase, DNase, pronase, and/or dispase, etc. Mechanical disruption can also be accomplished by a number of methods including, but not limited to the use of grinders, blenders, sieves, homogenizers, pressure cells, or insonators to name but a few. In one aspect, excised foreskin tissue is treated using digestive enzymes, typically collagenase and/or trypsinase to disassociate the cells from encapsulating structures.

The isolation of fibroblasts, for example, can be carried out as follows: fresh tissue samples are thoroughly washed and minced in Hanks' balanced salt solution (HBSS) in order to remove serum. The minced tissue is incubated from 1-12 hours in a freshly prepared solution of a dissociating enzyme such as trypsin. After such incubation, the dissociated cells are suspended, pelleted by centrifugation and plated onto culture dishes. All fibroblasts will attach before other cells, therefore, appropriate stromal cells can be selectively isolated and grown. The isolated fibroblasts can then be grown to confluency, lifted from the confluent culture and inoculated onto the three-dimensional framework, see Naughton et al., 1987, J. Med. 18(3&4):219-250. Inoculation of the three-dimensional framework with a high concentration of stromal cells, e.g., approximately $10^6$ to $5 \times 10^7$ cells/ml, will result in the establishment of the three-dimensional stromal support in shorter periods of time.

Once the tissue has been reduced to a suspension of individual cells, the suspension can be fractionated into subpopulations from which the fibroblasts and/or other stromal cells and/or elements can be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counter-streaming centrifugation), unit gravity separation, countercurrent distribution, electrophoresis and fluorescence-activated cell sorting. For a review of clonal selection and cell separation techniques, see Freshney, Culture of Animal Cells. A Manual of Basic Techniques, 2d Ed., A. R. Liss, Inc., New York, 1987, Ch. 11 and 12, pp. 137-168.

In one aspect, isolated fibroblast cells can be grown to produce cell banks. Cell banks are created to allow for initiating various quantities and timing of cultivation batches and to allow preemptive testing of cells for contaminants and specific cellular characteristics. Fibroblasts from the cell banks are subsequently grown to increase cell number to appropriate levels for seeding scaffolds. Operations involving environmental exposure of cells and cell contacting materials are performed by aseptic practices to reduce the potential for contamination of foreign materials or undesirable microbes.

In another aspect of the invention, after isolation, cells can be grown through several passages to a quantity suitable for building master cell banks. The cell banks can then be, harvested and filled into appropriate vessels and preserved in cryogenic conditions. Cells in frozen vials from master cell banks can be thawed and grown through additional passages (usually two or more). The cells can then be used to prepare cryogenically preserved working cell banks.

A cell expansion step uses vials of cells at the working cell bank stage to further increase cell numbers for inoculating three-dimensional scaffolds or supports, such as mesh or microcarriers. Each passage is a series of sub-culture steps that include inoculating cell growth surfaces, incubation, feeding the cells and harvesting.

Cultivation for cell banks and cell expansion can be conducted by inoculating culture vessels, such as culture flasks, roller bottles or microcarriers. Stromal cells, such as fibroblasts, attach to the intended growth surfaces and grow in the presence of culture media. Culture vessels, such as culture flasks, roller bottles and microcarriers are specifically configured for cell culture and are commonly made from various plastic materials qualified for intended applications. Microcarriers typically are microscopic or macroscopic beads and are typically made of various plastic materials. However, they can be made from other materials such as glasses or solid/semi-solid biologically based materials such as collagens or other materials such as Dextran, a modified sugar complex as discussed above.

During cultivation, expended media is periodically replaced with fresh media during the course of cell growth to maintain adequate availability of nutrients and removal of inhibitory products of cultivation. Culture flasks and roller bottles provide a surface for the cells to grow onto and are typically used for cultivation of anchorage dependent cells.

In one aspect, incubation is performed in a chamber heated at 37° C. Cultivation topologies requiring communication of media and the chamber environment use a 5% $CO_2$ v/v with air in the chamber gas space to aid in regulation of pH. Alternately, vessels equipped to maintain cultivation temperature and pH can be used for both cell expansion and ECM production operations. Temperatures below 35° C. or above 38° C. and $CO_2$ concentrations below 3% or above 12% may not be appropriate.

Harvesting cells from attachment surfaces can conducted by removal of growth media and rinsing the cells with a buffered salt solution to reduce enzyme competing protein, application of disassociating enzymes then neutralization of the enzymes after cell detachment. Harvested cell suspension is collected and harvest fluids are separated by centrifugation. Cell suspensions from sub-culture harvests can be sampled to assess the quantity of cells recovered and other cellular attributes and are subsequently combined with fresh media and applied as inoculums. The number of passages used for preparing cell banks and scaffold inoculum is critical with regard to achieving acceptable ECM characteristics.

After an appropriate two- or three-dimensional scaffold is prepared, it is inoculated by seeding with the prepared stromal cells. Inoculation of the scaffold may be done in a variety of ways, such as sedimentation. Mesh prepared for culture of ECM under aerobic conditions are prepared in the same manner as for hypoxic grown mesh with the exception that an anaerobic chamber is not used to create hypoxic conditions.

For example, for both mesh prepared for culture of ECM under both aerobic and hypoxic conditions, prepared and sterilized mesh is placed in sterile 150 mm diameter×15 mm deep petri dishes and stacked to a thickness of approximately 10 pieces. Stacks of mesh are then inoculated by sedimentation. Cells are added to fresh media to obtain the appropriate concentration of cells for inoculum. Inoculum is added to the stack of mesh where cells settle onto the nylon fibers and attach while in incubated conditions. After an adequate time, individually seeded mesh sheets can be aseptically separated from the stack and placed individually into separate 150 mm×15 mm petri dishes containing approximately 50 ml of growth media.

Incubation of the inoculated culture is performed under hypoxic conditions, which is discovered to produce an ECM and surrounding media with unique properties as compared to ECM generated under normal culture conditions. As used herein, hypoxic conditions are characterized by a lower oxygen concentration as compared to the oxygen concentration of ambient air (approximately 15%-20% oxygen). In one aspect, hypoxic conditions are characterized by an oxygen concentration less than about 10%. In another aspect hypoxic conditions are characterized by an oxygen concentration of about 1% to 10%, 1% to 9%, 1% to 8%, 1% to 7%, 1% to 6%, 1% to 5%, 1% to 4%, 1% to 3%, or 1% to 2%. In a certain aspect, the system maintains about 1-3% oxygen within the culture vessel. Hypoxic conditions can be created and maintained by using a culture apparatus that allows one to control ambient gas concentrations, for example, an anaerobic chamber.

Incubation of cell cultures is typically performed in normal atmosphere with 15-20% oxygen and 5% $CO_2$ for expansion and seeding, at which point low oxygen cultures are split to an airtight chamber that is flooded with 95% nitrogen/5% $CO_2$ so that a hypoxic environment is created within the culture medium.

For example, petri dishes with mesh cultured for producing ECM under hypoxic conditions are initially grown in incubation at 37° C. and 95% air/5% $CO_2$ for 2-3 weeks. Following the period of near atmospheric cultivation, the petri dishes of mesh are incubated in a chamber designed for anaerobic cultivation that is purged with a gas mixture of approximately 95% nitrogen and 5% $CO_2$. Expended growth media is replaced with fresh media at atmospheric oxygen level through the culture period and after media is exchanged the mesh filled petri dishes are place in the anaerobic chamber, the chamber is purged with 95% nitrogen/5% $CO_2$ then incubated at 37° C. Cultured mesh are harvested when they reach the desired size or contain the desire biological components.

During the incubation period, the stromal cells will grow linearly along and envelop the three-dimensional framework before beginning to grow into the openings of the framework. The growing cells produce a myriad of growth factors, regulatory factors and proteins, some of which are secreted in the surrounding media, and others that are deposited on the support to make up the extracellular matrix more fully discussed below. Growth and regulatory factors can be added to the culture, but are not necessary. Culture of the stromal cells produces both non-soluble and soluble fractions. The cells are grown to an appropriate degree to allow for adequate deposition of extracellular matrix proteins.

During culturing of the three-dimensional tissues, proliferating cells may be released from the framework and stick to the walls of the culture vessel where they may continue to proliferate and form a confluent monolayer. To minimize this occurrence, which may affect the growth of cells, released cells may be removed during feeding or by transferring the cell culture to a new culture vessel. Removal of the confluent monolayer or transfer of the cultured tissue to fresh media in a new vessel maintains or restores proliferative activity of the cultures. In some aspects, removal or transfers may be done in a culture vessel which has a monolayer of cultured cells exceeding 25% confluency. Alternatively, the culture in some embodiments is agitated to prevent the released cells from sticking; in others, fresh media is infused continuously through the system. In some aspects, two or more cell types can be cultured together either at the same time or one first followed by the second (e.g., fibroblasts and smooth muscle cells or endothelial cells).

After inoculation of the scaffolds, the cell culture is incubated in an appropriate nutrient medium and incubation conditions that supports growth of cells into the three dimensional tissues. Many commercially available media such as Dulbecco's Modified Eagles Medium (DMEM), RPMI 1640, Fisher's, Iscove's, and McCoy's, may be suitable for supporting the growth of the cell cultures. The medium may be supplemented with additional salts, carbon sources, amino acids, serum and serum components, vitamins, minerals, reducing agents, buffering agents, lipids, nucleosides, antibiotics, attachment factors, and growth factors. Formulations for different types of culture media are described in various reference works available to the skilled artisan (e.g., Methods for Preparation of Media, Supplements and Substrates for Serum Free Animal Cell Cultures, Alan R. Liss, New York (1984); Tissue Culture: Laboratory Procedures, John Wiley & Sons, Chichester, England (1996); Culture of Animal Cells, A Manual of Basic Techniques, 4th Ed., Wiley-Liss (2000)).

The growth or culture media used in any of the culturing steps of the present invention, whether under aerobic or hypoxic conditions, may include serum, or be serum free. In one aspect, the media is Dulbecco's Modified Eagle Medium with 4.5 g/L glucose, alanyl-L-glutamine, Eq 2 mM, and nominally supplemented with 10% fetal bovine serum. In another aspect, the media is a serum free media and is Dulbecco's Modified Eagle Medium with 4.5 g/L glucose base medium with Glutamax®, supplemented with 0.5% serum albumin, 2 µg/ml heparin, 1 µg/ml recombinant basic FGF, 1 µg/ml soybean trypsin inhibitor, 1× ITS supplement (insulin-transferrin-selenium, Sigma Cat. No. 13146), 1:1000 diluted fatty acid supplement (Sigma Cat. No. 7050), and 1:1000 diluted cholesterol. Additionally, the same media can be used for both hypoxic and aerobic cultivation. In one aspect, the growth media is changed from serum based media to serum free media after seeding and the first week of growth.

Incubation conditions will be under appropriate conditions of pH, temperature, and gas (e.g., $O_2$, $CO_2$, etc) to maintain an hypoxic growth condition. In some embodiments, the cell culture can be suspended in the medium during the incubation period in order to maximize proliferative activity and generate factors that facilitate the desired biological activities of the fractions. In addition, the culture may be "fed" periodically to remove the spent media, depopulate released cells, and add new nutrient source. During the incubation period, the cultured cells grow linearly along and envelop the filaments of the scaffold before beginning to grow into the openings of the scaffold.

During incubation under hypoxic conditions, as compared to incubation under normal atmospheric oxygen concentrations of about 15-20%, thousands of genes are differentially expressed. Several genes have been found to be upregulated or downregulated in such compositions, most notably certain laminin species, collagen species and Wnt factors. In various aspects, the three dimensional extracellular matrix may be defined by the characteristic fingerprint or suite of cellular products produced by the cells due to growth in hypoxic condition as compared with growth under normal conditions. In the extracellular matrix compositions specifically exemplified herein, the three-dimensional tissues and surrounding media are characterized by expression and/or secretion of various factors.

The three dimensional tissues and compositions described herein have extracellular matrix that is present on the scaffold or framework. In some aspects, the extracellular matrix includes various laminin and collagen types due to growth under hypoxic conditions and selection of cells grown on the support. The proportions of extracellular matrix (ECM) proteins deposited can be manipulated or enhanced by selecting fibroblasts which elaborate the appropriate collagen type as well as growing the cells under hypoxic conditions in which expression of specific laminin and collagen species are upregulated or downregulated.

Selection of fibroblasts can be accomplished in some aspects using monoclonal antibodies of an appropriate isotype or subclass that define particular collagen types. In other aspects, solid substrates, such as magnetic beads, may be used to select or eliminate cells that have bound antibody. Combination of these antibodies can be used to select (positively or negatively) the fibroblasts which express the desired collagen type. Alternatively, the stroma used to inoculate the framework can be a mixture of cells which synthesize the desired collagen types. The distribution and origins of the exemplary type of collagen are shown in Table I.

TABLE 1

Distributions and Origins of Various Types of Collagen

| Collagen Type | Principle Tissue Distribution | Cells of Origin |
|---|---|---|
| I | Loose and dense ordinary connective tissue; collagen fibers | Fibroblasts and reticular cells; smooth muscle cells |
|  | Fibrocartilage |  |
|  | Bone | Osteoblasts |
|  | Dentin | Odontoblasts |
| II | Hyaline and elastic cartilage | Chondrocytes |
|  | Vitreous body of eye | Retinal cells |
| III | Loose connective tissue; reticular fibers | Fibroblasts and reticular cells |
|  | Papillary layer of dermis | Smooth muscle cells; endothelial cells |
|  | Blood vessels |  |
| IV | Basement membranes | Epithelial and endothelial cells |
|  | Lens capsule of eye | Lens fibers |
| V | Fetal membranes; placenta | Fibroblasts |
|  | Basement membranes |  |
|  | Bone |  |
|  | Smooth muscle | Smooth muscle cells |
| IV | Basement membranes | Epithelial and endothelial cells |
|  | Lens capsule of the eye | Lens fiber |
| V | Fetal membranes; placenta | Fibroblasts |
|  | Basement membranes |  |
|  | Bone |  |
|  | Smooth muscle | Smooth muscle cells |
| VI | Connective tissue | Fibroblasts |
| VII | Epithelial basement membranes | Fibroblasts |
|  | anchoring fibrils | keratinocytes |
| VIII | Cornea | Corneal fibroblasts |
| IX | Cartilage |  |
| X | Hypertrophic cartilage |  |
| XI | Cartilage |  |
| XII | Papillary dermis | Fibroblasts |
| XIV (undulin) | Reticular dermis | Fibroblasts |
| XVII | P170 bullous pemphigoid antigen | Keratinocytes |

Additional types of collagen that may be present in ECM compositions are shown in Table 2.

TABLE 2

Types of Collagen and Corresponding Gene(s)

| Collagen Type | Gene(s) |
|---|---|
| I | COL1A1, COL1A2 |
| II | COL2A1 |
| III | COL3A1 |
| IV | COL4A1, COL4A2, COL4A3, COL4A4, COL4A5, COL4A6 |
| V | COL5A1, COL5A2, COL5A3 |
| VI | COL6A1, COL6A2, COL6A3 |
| VII | COL7A1 |
| VIII | COL8A1, COL8A2 |
| IX | COL9A1, COL9A2, COL9A3 |
| X | COL10A1 |
| XI | COL11A1, COL11A2 |
| XII | COL12A1 |
| XIII | COL13A1 |
| XIV | COL14A1 |
| XV | COL15A1 |
| XVI | COL16A1 |
| XVII | COL17A1 |
| XVIII | COL18A1 |
| XIX | COL19A1 |
| XX | COL20A1 |
| XXI | COL21A1 |
| XXII | COL22A1 |
| XXIII | COL23A1 |
| XXIV | COL24A1 |
| XXV | COL25A1 |
| XXVI | EMID2 |
| XXVII | COL27A1 |
| XXVIII | COL28A1 |

As discussed above the ECM compositions described herein include various collagens. As shown in Table 3 of Example 1, expression of several species of collagen are found to be upregulated in hypoxic cultured ECM compositions. Accordingly, in one aspect of the present invention, the ECM composition including one or more embryonic proteins, includes upregulation of collagen species as compared with that produced in oxygen conditions of about 15-20% oxygen. In another aspect, the upregulated collagen species are type V alpha 1; IX alpha 1; IX alpha 2; VI alpha 2; VIII alpha 1; IV, alpha 5; VII alpha 1; XVIII alpha 1; and XII alpha 1.

In addition to various collagens, the ECM composition described herein include various laminins. Laminins are a family of glycoprotein heterotrimers composed of an alpha, beta, and gamma chain subunit joined together through a coiled-coil domain. To date, 5 alpha, 4 beta, and 3 gamma laminin chains have been identified that can combine to form 15 different isoforms. Within this structure are identifiable domains that possess binding activity towards other laminin and basal lamina molecules, and membrane-bound receptors. Domains VI, IVb, and IVa form globular structures, and domains V, IIIb, and IIIa (which contain cysteine-rich EGF-like elements) form rod-like structures. Domains I and II of the three chains participate in the formation of a triple-stranded coiled-coil structure (the long arm).

Laminin chains possess shared and unique functions and are expressed with specific temporal (developmental) and spatial (tissue-site specific) patterns. The laminin alpha-chains are considered to be the functionally important portion of the heterotrimers, as they exhibit tissue-specific distribution patterns and contain the major cell interaction sites. Vascular endothelium is known to express two laminin isoforms, with varied expression depending on the developmental stage, vessel type, and the activation state of the endothelium.

Accordingly, in one aspect of the present invention, the ECM composition including one or more embryonic proteins, includes upregulation or downregulation of various laminin species as compared with that produced in oxygen conditions of about 15-20% oxygen.

Laminin 8, is composed of alpha-4, beta-1, and gamma-1 laminin chains. The laminin alpha-4 chain is widely distributed both in adults and during development. In adults it can be identified in the basement membrane surrounding cardiac, skeletal, and smooth muscle fibers, and in lung alveolar septa. It is also known to exist in the endothelial basement membrane both in capillaries and larger vessels, and in the perineurial basement membrane of peripheral nerves, as well as in intersinusoidal spaces, large arteries, and smaller arterioles of bone marrow Laminin 8 is a major laminin isoform in the vascular endothelium that is expressed and adhered to by platelets and is synthesized in 3T3-L1 adipocytes, with its level of synthesis shown to increase upon adipose conversion of the cells. Laminin 8 is thought to be the laminin isoform generally expressed in mesenchymal cell lineages to induce microvessels in connective tissues. Laminin 8 has also been identified in mouse bone marrow primary cell cultures, arteriolar walls, and intersinusoidal spaces where it is the major laminin isoform in the developing bone marrow. Due to its localization in adult bone marrow adjacent to hematopoietic cells, laminin isoforms containing the alpha-4 chain are likely to have biologically relevant interactions with developing hematopoietic cells.

Accordingly, in another aspect of the present invention the ECM includes upregulation of laminin species, such as laminin 8. In another aspect, laminins produced by the three dimensional tissues of the present invention, includes at least laminin 8, which defines a characteristic or signature of the laminin proteins present in the composition.

The ECM compositions described herein include various Wnt factors. Wnt family factors are signaling molecules having roles in a myriad of cellular pathways and cell-cell interaction processes. Wnt signaling has been implicated in tumorigenesis, early mesodermal patterning of the embryo, morphogenesis of the brain and kidneys, regulation of mammary gland proliferation, and Alzheimer's disease. As shown in Table 4 of Example 1, expression of several species of Wnt proteins are found to be upregulated in hypoxic cultured ECM compositions. Accordingly, in one aspect of the present invention, the ECM composition including one or more embryonic proteins, includes upregulation of Wnt species as compared with that produced in oxygen conditions of about 15-20% oxygen. In another aspect, the upregulated Wnt species are Wnt 7a and Wnt 11. In another aspect, Wnt factors produced by the three dimensional tissues of the present invention, include at least Wnt7a, and Wnt11, which defines a characteristic or signature of the Wnt proteins present in the composition.

A discussed throughout, the ECM compositions of the present invention includes both soluble and non-soluble fractions or any portion thereof. It is to be understood that the compositions of the present invention may include either or both fractions, as well as any combination thereof. Additionally, individual components may be isolated from the fractions to be used individually or in combination with other isolates or known compositions.

Accordingly, in various aspects, extracellular matrix compositions produced using the methods of the present invention may be used directly or processed in various ways, the methods of which may be applicable to both the non-soluble and soluble fractions. The soluble fraction, including the cell-free supernatant and media, may be subject to lyophilization for preserving and/or concentrating the factors. Various biocompatible preservatives, cryoprotectives, and stabilizer agents may be used to preserve activity where required. Examples of biocompatible agents include, among others, glycerol, dimethyl sulfoxide, and trehalose. The lyophilizate may also have one or more excipients such as buffers, bulking agents, and tonicity modifiers. The freeze-dried media may be reconstituted by addition of a suitable solution or pharmaceutical diluent, as further described below.

In other aspects, the soluble fraction is dialyzed. Dialysis is one of the most commonly used techniques to separate sample components based on selective diffusion across a porous membrane. The pore size determines molecular-weight cutoff (MWCO) of the membrane that is characterized by the molecular-weight at which 90% of the solute is retained by the membrane. In certain aspects membranes with any pore size is contemplated depending on the desired cutoff. Typical cutoffs are 5,000 Daltons, 10,000 Daltons, 30,000 Daltons, and 100,000 Daltons, however all sizes are contemplated.

In some aspects, the soluble fraction may be processed by precipitating the active components (e.g., growth factors) in the media. Precipitation may use various procedures, such as salting out with ammonium sulfate or use of hydrophilic polymers, for example polyethylene glycol.

In other aspects, the soluble fraction is subject to filtration using various selective filters. Processing the soluble fraction by filtering is useful in concentrating the factors present in the fraction and also removing small molecules and solutes used in the soluble fraction. Filters with selectivity for specified molecular weights include <5000 Daltons, <10,000 Daltons, and <15,000 Daltons. Other filters may be used and the processed media assayed for therapeutic activity as described herein. Exemplary filters and concentrator system include those based on, among others, hollow fiber filters, filter disks, and filter probes (see, e.g., Amicon Stirred Ultrafiltration Cells).

In still other aspects, the soluble fraction is subject to chromatography to remove salts, impurities, or fractionate various components of the medium. Various chromatographic techniques may be employed, such as molecular sieving, ion exchange, reverse phase, and affinity chromatographic techniques. For processing conditioned medium without significant loss of bioactivity, mild chromatographic media may be used. Non-limiting examples include, among others, dextran, agarose, polyacrylamide based separation media (e.g., available under various tradenames, such as Sephadex, Sepharose, and Sephacryl).

In still other aspects, the conditioned media is formulated as liposomes. The growth factors may be introduced or encapsulated into the lumen of liposomes for delivery and for extending life time of the active factors. As known in the art, liposomes can be categorized into various types: multilamellar (MLV), stable plurilamellar (SPLV), small unilamellar (SUV) or large unilamellar (LUV) vesicles. Liposomes can be prepared from various lipid compounds, which may be synthetic or naturally occurring, including phosphatidyl ethers and esters, such as phosphotidylserine, phosphotidylcholine, phosphatidyl ethanolamine, phosphatidylinositol, dimyristoylphosphatidylcholine; steroids such as cholesterol; cerebrosides; sphingomyelin; glycerolipids; and other lipids (see, e.g., U.S. Pat. No. 5,833,948).

The soluble fraction may be used directly without additional additives, or prepared as pharmaceutical compositions with various pharmaceutically acceptable excipients, vehicles or carriers. A "pharmaceutical composition" refers to a form of the soluble and/or non-soluble fractions and at least one pharmaceutically acceptable vehicle, carrier, or excipient. For intradermal, subcutaneous or intramuscular administration, the compositions may be prepared in sterile suspension, solutions or emulsions of the extracellular matrix compositions in aqueous or oily vehicles. The compositions may also contain formulating agents, such as suspending, stabilizing or dispersing agents. Formulations for injection may be presented in unit dosage form, ampules in multidose containers, with or without preservatives. Alternatively, the compositions may be presented in powder form for reconstitution with a suitable vehicle including, by way of example and not limitation, sterile pyrogen free water, saline, buffer, or dextrose solution.

In other aspects, the three dimensional tissues are cryopreserved preparations, which are thawed prior to use. Pharmaceutically acceptable cryopreservatives include, among others, glycerol, saccharides, polyols, methylcellulose, and dimethyl sulfoxide. Saccharide agents include monosaccharides, disaccharides, and other oligosaccharides with glass transition temperature of the maximally freeze-concentrated solution (Tg) that is at least −60,−50,−40,−30,−20,−10, or 0° C. An exemplary saccharide for use in cryopreservation is trehalose.

In some aspects, the three dimensional tissues are treated to kill the cells prior to use. In some aspects, the extracellular matrix deposited on the scaffolds may be collected and processed for administration (see U.S. Pat. Nos. 5,830,708 and 6,280,284, incorporated herein by reference).

In other embodiments, the three dimensional tissue may be concentrated and washed with a pharmaceutically acceptable medium for administration. Various techniques for concentrating the compositions are available in the art, such as centrifugation or filtering. Examples include, dextran sedimentation and differential centrifugation. Formulation of the three dimensional tissues may also involve adjusting the ionic strength of the suspension to isotonicity (i.e., about 0.1 to 0.2) and to physiological pH (i.e., pH 6.8 to 7.5). The formulation may also contain lubricants or other excipients to aid in administration or stability of the cell suspension. These include, among others, saccharides (e.g., maltose) and organic polymers, such as polyethylene glycol and hyaluronic acid. Additional details for preparation of various formulations are described in U.S. Patent Publication No. 2002/0038152, incorporated herein by reference.

As discussed above, the ECM compositions of the present invention may be processed in a number of ways depending on the anticipated application and appropriate delivery or administration of the ECM composition. For example, the compositions may be delivered as three-dimensional scaffolds or implants, or the compositions may be formulated for injection as described above. The terms "administration" or "administering" are defined to include an act of providing a compound or pharmaceutical composition of the invention to a subject in need of treatment. The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion. The phrases "systemic administration," "administered systemically," "peripheral administration" and "administered peripherally" as used herein mean the administration of a compound, drug or other material other than directly into the central nervous system, such that it enters the subject's system and, thus, is subject to metabolism and other like processes, for example, subcutaneous administration.

The term "subject" as used herein refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

The extracellular matrix compositions of the present invention have a variety of applications including, but not limited to, promoting repair and/or regeneration of damaged cells or tissues, use in patches to promote tissue regeneration, use in tissue culture systems for culturing cells, such as stem cells, use in surface coatings used in association with implantable devices (e.g., pacemakers, stents, stent grafts, vascular prostheses, heart valves, shunts, drug delivery ports or catheters), promoting soft tissue repair, augmentation, and/or improvement of a skin surface, such as wrinkles, use as a biological anti-adhesion agent or as a biological vehicle for cell delivery or maintenance at a site of delivery.

Additionally, the ECM compositions derived from culturing cells as described in any method herein, may be used in any other application or method of the present invention. For example, the ECM compositions generated by culturing cells using the tissue culture system of the present invention may be used, for example, in the repair and/or regeneration of cells, use in patches to promote tissue regeneration, use in tissue culture systems for culturing cells, such as stem cells, use in surface coatings used in association with implantable devices (e.g., pacemakers, stents, stent grafts, vascular prostheses, heart valves, shunts, drug delivery ports or catheters), promoting soft tissue repair, augmentation, and/or improvement of a skin surface, such as wrinkles, use as a biological anti-adhesion agent or as a biological vehicle for cell delivery or maintenance at a site of delivery.

In various embodiments, the present invention includes methods for repair and/or regeneration of cells or tissue and promoting soft tissue repair. One embodiment includes a method of repair and/or regeneration of cells by contacting cells to be repaired or regenerated with the extracellular matrix compositions of the present invention. The method may be used for repair and/or regeneration of a variety of cells as discussed herein, including osteochondral cells.

In one aspect, the method contemplates repair of osteochondral defects. As used herein, "osteochondral cells" refers to cells which belong to either the chondrogenic or osteogenic lineage or which can undergo differentiation into either the chondrogenic or osteogenic lineage, depending on the environmental signals. This potential can be tested in vitro or in vivo by known techniques. Thus, in one aspect, the ECM compositions of the present invention are used to repair and/or regenerate, chondrogenic cells, for example, cells which are capable of producing cartilage or cells which themselves differentiate into cells producing cartilage, including chondrocytes and cells which themselves differentiate into chondrocytes (e.g., chondrocyte precursor cells). Thus, in another aspect, the compositions of the present invention are useful in repair and/or regeneration of connective tissue. As used herein, "connective tissue" refers to any of a number of structural tissues in the body of a mammal including but not limited to bone, cartilage, ligament, tendon, meniscus, dermis, hypodermis, muscle, fatty tissue, joint capsule.

The ECM compositions of the present invention may be used for treating osteochondral defects of a diarthroidal joint, such as knee, an ankle, an elbow, a hip, a wrist, a knuckle of either a finger or toe, or a temperomandibular joint. Such osteochondral defects can be the result of traumatic injury (e.g., a sports injury or excessive wear) or a disease such as osteoarthritis. A particular aspect relates to the use of the matrix of the present invention in the treatment or prevention of superficial lesions of osteoarthritic cartilage. Additionally the present invention is of use in the treatment or prevention of osteochondral defects which result from ageing or from giving birth. Osteochondral defects in the context of the present invention should also be understood to comprise those conditions where repair of cartilage and/or bone is required in the context of surgery such as, but not limited to, cosmetic surgery (e.g., nose, ear). Thus such defects can occur anywhere in the body where cartilage or bone formation is disrupted or where cartilage or bone are damaged or non-existent due to a genetic defect.

As discussed above, growth factors or other biological agents which induce or stimulate growth of particular cells may be included in the ECM compositions of the present invention. The type of growth factors will be dependent on the cell-type and application for which the composition is intended. For example, in the case of osteochondral cells, additional bioactive agents may be present such as cellular growth factors (e.g., TGF-β), substances that stimulate chondrogenesis (e.g., BMPs that stimulate cartilage formation such as BMP-2, BMP-12 and BMP-13), factors that stimulate migration of stromal cells to the scaffold, factors that stimulate matrix deposition, anti-inflammatories (e.g., non-steroidal anti-inflammatories), immunosuppressants (e.g., cyclosporins). Other proteins may also be included, such as other growth factors such as platelet derived growth factors (PDGF), insulin-like growth factors (IGF), fibroblast growth factors (FGF), epidermal growth factor (EGF), human endothelial cell growth factor (ECGF), granulocyte macrophage colony stimulating factor (GM-CSF), vascular endothelial growth factor (VEGF), cartilage derived morphogenetic protein (CDMP), other bone morphogenetic proteins such as OP-1, OP-2, BMP3, BMP4, BMP9, BMP11, BMP14, DPP, Vg-1, 60A, and Vgr-1, collagens, elastic fibers, reticular fibers, glycoproteins or glycosaminoglycans, such as heparin sulfate, chondroitin-4-sulfate, chondroitin-6-sulfate, dermatan sulfate, keratin sulfate, etc. For example, growth factors such as TGF-β, with ascorbate, have been found to trigger chondrocyte differentiation and cartilage formation by chondrocytes. In addition, hyaluronic acid is a good substrate for the attachment of chondrocytes and other stromal cells and can be incorporated as part of the scaffold or coated onto the scaffold.

Additionally, other factors which influence the growth and/or activity of particular cells may also be used. For example, in the case of chondrocytes, a factor such as a chondroitinase which stimulates cartilage production by chondrocytes can be added to the matrix in order to maintain chondrocytes in a hypertrophic state as described in U.S. Patent Application No. 2002/0122790 incorporated herein by reference. In another aspect, the methods of the present invention include the presence of polysulphated alginates or other polysulphated polysaccharides such as polysulphated cyclodextrin and/or polysulphated inulin, or other components capable of stimulating production of extracellular matrix of connective tissue cells as described in International Patent Publication No. WO 2005/054446 incorporated herein by reference.

The cell or tissue to be repaired and/or regenerated may be contacted in vivo or in vitro by any of the methods described herein. For example, the ECM compositions may be injected or implanted (e.g., via ECM tissue, a patch or coated device of the present invention) into the subject. In another aspect, the tissue or cells to be repaired and/or regenerated may be harvested from the subject and cultured in vitro and subsequently implanted or administered to the subject using known surgical techniques.

As discussed above, the ECM compositions of the present invention may be processed in a variety of ways. Accordingly, in one embodiment, the present invention includes a tissue culture system. In various aspects, the culture system is composed of the extracellular matrix compositions described herein. The ECM compositions of the present invention may be incorporated into the tissue culture system in a variety of ways. For example, compositions may be incorporated as coatings, by impregnating three-dimensional scaffold materials as described herein, or as additives to media for culturing cells. Accordingly, in one aspect, the culture system can include three-dimensional support materials impregnated with any of the extracellular matrix compositions described herein, such as growth factors or embryonic proteins.

The extracellular matrix compositions described herein may serve as a support or three-dimensional support for the growth of various cell types. Any cell type capable of cell culture is contemplated. In one aspect, the culture system can be used to support the growth of stem cells. In another aspect, the stem cells are embryonic stem cells, mesenchymal stem cells or neuronal stem cells.

The tissue culture system may be used for generating additional ECM compositions, such as implantable tissue. Accordingly, culturing of cells using the tissue culture system of the present invention may be performed in vivo or in vitro. For example, the tissue culture system of the present invention may be used to generate ECM compositions for injection or implantation into a subject. The ECM compositions generated by the tissue culture system may be processed and used in any method described herein.

The ECM compositions of the present invention may be used as a biological vehicle for cell delivery. As described herein, the ECM compositions may include both soluble and/or non-soluble fractions. As such, in another embodiment of the present invention, a biological vehicle for cell delivery or maintenance at a site of delivery including the extracellular matrix compositions of the present invention, is described. The ECM compositions of the present invention, including cells and three-dimensional tissue compositions, may be used to promote and/or support growth of cells in vivo. The vehicle can be used in any appropriate application, for example to support injections of cells, such as stem cells, into damaged heart muscle or for tendon and ligament repair as described above.

Appropriate cell compositions (e.g., isolated ECM cells of the present invention and/or additional biological agents) can be administered before, after or during the ECM compositions are implanted or administered. For example, the cells can be seeded into the site of administration, defect, and/or implantation before the culture system or biological delivery vehicle is implanted into the subject. Alternatively, the appropriate cell compositions can be administered after (e.g., by injection into the site). The cells act therein to induce tissue regeneration and/or cell repair. The cells can be seeded by any means that allows administration of the cells to the defect site, for example, by injection. Injection of the cells can be by any means that maintains the viability of the cells, such as, by syringe or arthroscope.

Extracellular matrix compositions have been described for promoting angiogenesis in organs and tissues by administering such compositions to promote endothelialization and vascularization in the heart and related tissues. Accordingly, in yet another embodiment, the present invention includes a surface coating used in association with implantation of a device in a subject including the extracellular matrix compositions described herein. The coating may be applied to any device used in implantation or penetration of a subject, such as a pacemaker, a stent, a stent graft, a vascular prosthesis, a heart valve, a shunt, a drug delivery port or a catheter. In certain aspects, the coating can be used for modifying wound healing, modifying inflammation, modifying a fibrous capsule formation, modifying tissue ingrowth, or modifying cell ingrowth. In another embodiment, the present invention includes a for treatment of damaged tissue, such as heart, intestinal, infarcted or ischemic tissue. Presented below are examples discussing generation of extracellular matrix compositions contemplated for such applications. The preparation and use of extracellular matrix compositions grown under normal oxygen conditions is described in U.S. Patent Application No. 2004/0219134 incorporated herein by reference.

In another embodiment, the present invention includes a tissue regeneration patch including the extracellular matrix compositions described herein. In another embodiment the present invention includes a method for improvement of a skin surface in a subject including administering to the subject at the site of a wrinkle, the extracellular matrix compositions described herein. In yet another embodiment, the present invention includes a method for soft tissue repair or augmentation in a subject including administering to the subject at the site of a wrinkle, the extracellular matrix compositions described herein. The preparation and use of extracellular matrix compositions created under normal oxygen culture conditions for the repair and/or regeneration of cells, improvement of skin surfaces, and soft tissue repair are described in U.S. Pat. No. 5,830,708, U.S. Pat. No. 6,284,284, U.S. Patent Application No. 2002/0019339 and U.S. Patent Application No. 2002/0038152 incorporated herein by reference.

In another embodiment, the present invention includes a biological anti-adhesion agent including the extracellular matrix compositions described herein. The agent can be used in such applications as anti-adhesion patches used after the creation of intestinal or blood vessel anastomises.

The compositions or active components used herein, will generally be used in an amount effective to treat or prevent the particular disease being treated. The compositions may be administered therapeutically to achieve therapeutic benefit or prophylactically to achieve prophylactic benefit. By therapeutic benefit is meant eradication or amelioration of the underlying condition or disorder being treated. Therapeutic benefit also includes halting or slowing the progression of the disease, regardless of whether improvement is realized.

The amount of the composition administered will depend upon a variety of factors, including, for example, the type of composition, the particular indication being treated, the mode of administration, whether the desired benefit is prophylactic or therapeutic, the severity of the indication being treated and the age and weight of the patient, and effectiveness of the dosage form. Determination of an effective dosage is well within the capabilities of those skilled in the art.

Initial dosages may be estimated initially from in vitro assays. Initial dosages can also be estimated from in vivo data, such as animal models. Animals models useful for testing the efficacy of compositions for enhancing hair growth include, among others, rodents, primates, and other mammals. The skilled artisans can determine dosages suitable for human administration by extrapolation from the in vitro and animal data.

Dosage amounts will depend upon, among other factors, the activity of the conditioned media, the mode of administration, the condition being treated, and various factors discussed above. Dosage amount and interval may be adjusted individually to provide levels sufficient to the maintain the therapeutic or prophylactic effect.

In one embodiment, the methods of the invention include administration of the ECM in combination with an anti-inflammatory agent, antihistamines, chemotherapeutic agent, immunomodulator, therapeutic antibody or a protein kinase inhibitor, to a tissue, cell or subject in need of such treatment. While not wanting to be limiting, chemotherapeutic agents include antimetabolites, such as methotrexate, DNA cross-linking agents, such as cisplatin/carboplatin; alkylating agents, such as canbusil; topoisomerase I inhibitors such as dactinomicin; microtubule inhibitors such as taxol (paclitaxol), and the like. Other chemotherapeutic agents include, for example, a vinca alkaloid, mitomycin-type antibiotic, bleomycin-type antibiotic, antifolate, colchicine, demecoline, etoposide, taxane, anthracycline antibiotic, doxorubicin, daunorubicin, carminomycin, epirubicin, idarubicin, mithoxanthrone, 4-dimethoxy-daunomycin, 11-deoxydaunorubicin, 13-deoxydaunorubicin, adriamycin-14-benzoate, adriamycin-14-octanoate, adriamycin-14-naphthaleneacetate, amsacrine, carmustine, cyclophosphamide, cytarabine, etoposide, lovastatin, melphalan, topetecan, oxalaplatin, chlorambucil, methtrexate, lomustine, thioguanine, asparaginase, vinblastine, vindesine, tamoxifen, or mechlorethamine. While not wanting to be limiting, therapeutic antibodies include antibodies directed against the HER2 protein, such as trastuzumab; antibodies directed against growth factors or growth factor receptors, such as bevacizumab, which targets vascular endothelial growth factor, and OSI-774, which targets epidermal growth factor; antibodies targeting integrin receptors, such as Vitaxin (also known as MEDI-522), and the like. Classes of anticancer agents suitable for use in compositions and methods of the present invention include, but are not limited to: 1) alkaloids, including, microtubule inhibitors (e.g., Vincristine, Vinblastine, and Vindesine, etc.), microtubule stabilizers (e.g., Paclitaxel [Taxol], and Docetaxel, Taxotere, etc.), and chromatin function inhibitors, including, topoisomerase inhibitors, such as, epipodophyllotoxins (e.g., Etoposide [VP-16], and Teniposide [VM-26], etc.), and agents that target topoisomerase I (e.g., Camptothecin and Isirinotecan [CPT-11], etc.); 2) covalent DNA-binding agents [alkylating agents], including, nitrogen mustards (e.g., Mechlorethamine, Chlorambucil, Cyclophosphamide, Ifosphamide, and Busulfan [Myleran], etc.), nitrosoureas (e.g., Carmustine, Lomustine, and Semustine, etc.), and other alkylating agents (e.g., Dacarbazine, Hydroxymethylmelamine, Thiotepa, and Mitocycin, etc.); 3) noncovalent DNA-binding agents [antitumor antibiotics], including, nucleic acid inhibitors (e.g., Dactinomycin [Actinomycin D], etc.), anthracyclines (e.g., Daunorubicin [Daunomycin, and Cerubidine], Doxorubicin [Adriamycin], and Idarubicin [Idamycin], etc.), anthracenediones (e.g., anthracycline analogues, such as, [Mitoxantrone], etc.), bleomycins (Blenoxane), etc., and plicamycin (Mithramycin), etc.; 4) antimetabolites, including, antifolates (e.g., Methotrexate, Folex, and Mexate, etc.), purine antimetabolites (e.g., 6-Mercaptopurine [6-MP, Purinethol], 6-Thioguanine [6-TG], Azathioprine, Acyclovir, Ganciclovir, Chlorodeoxyadenosine, 2-Chlorodeoxyadenosine [CdA], and 2'-Deoxycoformycin [Pentostatin], etc.), pyrimidine antagonists (e.g., fluoropyrimidines [e.g., 5-fluorouracil (Adrucil), 5-fluorodeoxyuridine (FdUrd) (Floxuridine)] etc.), and cytosine arabinosides (e.g., Cytosar [ara-C] and Fludarabine, etc.); 5) enzymes, including, L-asparaginase; 6) hormones, including, glucocorticoids, such as, antiestrogens (e.g., Tamoxifen, etc.), nonsteroidal antiandrogens (e.g., Flutamide, etc.), and aromatase inhibitors (e.g., anastrozole [Arimidex], etc.); 7) platinum compounds (e.g., Cisplatin and Carboplatin, etc.); 8) monoclonal antibodies conjugated with anticancer drugs, toxins, and/or radionuclides, etc.; 9) biological response modifiers (e.g., interferons [e.g., IFN-.alpha., etc.] and interleukins [e.g., IL-2, etc.], etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., Batimistat, etc.); and 17) inhibitors of angiogenesis.

The pharmaceutical composition and method of the present invention may further comprise other therapeutically active compounds as noted herein which are usually applied in the treatment of the above mentioned pathological conditions. Examples of other therapeutic agents include the following: cyclosporins (e.g., cyclosporin A), CTLA4-Ig, antibodies such as ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, such as antibodies specific for CD40 and/or gp39 (i.e., CD154), fusion proteins constructed from CD40 and gp39 (CD40Ig and CD8 gp39), inhibitors, such as nuclear translocation inhibitors, of NF-kappa B function, such as deoxyspergualin (DSG), cholesterol biosynthesis inhibitors such as HMG CoA reductase inhibitors (lovastatin and simvastatin), non-steroidal antiinflammatory drugs (NSAIDs) such as ibuprofen and cyclooxygenase inhibitors such as rofecoxib, steroids such as prednisone or dexamethasone, gold compounds, antiproliferative agents such as methotrexate, FK506 (tacrolimus, Prograf), mycophenolate mofetil, cytotoxic drugs such as azathioprine and cyclophosphamide, TNF-a inhibitors such as tenidap, anti-TNF antibodies or soluble TNF receptor, and rapamycin (sirolimus or Rapamune) or derivatives thereof.

Other agents that may be administered in combination with invention compositions and methods including protein therapeutic agents such as cytokines, immunomodulatory agents and antibodies. As used herein the term "cytokine" encompasses chemokines, interleukins, lymphokines, monokines, colony stimulating factors, and receptor associated proteins, and functional fragments thereof. As used herein, the term "functional fragment" refers to a polypeptide or peptide which possesses biological function or activity that is identified through a defined functional assay.

The cytokines include endothelial monocyte activating polypeptide II (EMAP-II), granulocyte-macrophage-CSF (GM-CSF), granulocyte-CSF (G-CSF), macrophage-CSF (M-CSF), IL-1, IL-2, IL-3, IL-4, IL-5, IL-6, IL-12, and IL-13, interferons, and the like and which is associated with a particular biologic, morphologic, or phenotypic alteration in a cell or cell mechanism.

When other therapeutic agents are employed in combination with the compositions or methods of the present invention they may be used for example in amounts as noted in the Physician Desk Reference (PDR) or as otherwise determined by one having ordinary skill in the art.

Presented below are examples discussing generation of extracellular matrix compositions contemplated for the discussed applications. The following examples are provided to further illustrate the embodiments of the present invention, but are not intended to limit the scope of the invention. While they are typical of those that might be used, other procedures, methodologies, or techniques known to those skilled in the art may alternatively be used.

Example 1

Differential Gene Expression in ECM Compositions Grown Under Hypoxic Conditions

Primary human neonatal foreskin fibroblasts were cultured as standard monolayers in tissue culture flasks and compared to three-dimensional fibroblast cultures, within a naturally deposited, fetal-like ECM. The cultures were grown as disclosed herein. To assess differential expression of genes, samples of total RNA were completed using Agilent Whole Human Genome Oligo Microarrays® for global gene expression (including less than 40,000 genes) following the manufacturer's protocol.

Upon comparison, fibroblasts were found to regulate collagen and ECM gene expression in three-dimensional cultures within a hypoxic cultured naturally secreted ECM. Upregulation and downregulation of expression of various collagen and ECM genes are evident in Table 3.

TABLE 3

Differential Collagen and ECM Expression in Hypoxic Three-Dimensional Fibroblast Cultures

| GENE | FOLD INCREASE | FOLD DECREASE |
|---|---|---|
| COL4A1 | 17.2 | |
| COL20A1 | 6.88 | |
| COL19A1 | 5.22 | |
| COL9A1 | 4.81 | |
| COL10A1 | 4.45 | |
| COL6A3 | 3.48 | |
| COL9A2 | 2.48 | |
| COL14A1 | 2 | |
| SPARC | 2.74 | |
| COL1A2 | | 3.45 |
| COL13A1 | | 4 |
| COL18A1 | | 4.76 |
| COL1A2 | | 7.14 |

Upon comparison, fibroblasts were found to regulate gene expression of Wnt pathway genes in three-dimensional cultures within a hypoxic cultured naturally secreted ECM. Upregulation and downregulation of expression of various Wnt pathway genes are evident in Table 4.

TABLE 4

Differential Wnt Expression in Hypoxic Three-dimensional Fibroblast Cultures

| GENE | FOLD INCREASE | FOLD DECREASE |
|---|---|---|
| WNT 4 | 5.94 | |
| WNT 7a | 5.43 | |
| WNT 7b | 4.05 | |
| WNT 2b | 3.95 | |
| WNT 10a | 3.86 | |

TABLE 4-continued

Differential Wnt Expression in Hypoxic
Three-dimensional Fibroblast Cultures

| GENE | FOLD INCREASE | FOLD DECREASE |
|---|---|---|
| WNT 8b | 3.48 | |
| WNT 6 | 3.36 | |
| WNT 3a | 3.19 | |
| WNT 9b | 3.06 | |
| WNT 9a | 3.02 | |
| WNT 11 | 2.89 | |
| WNT 5a | | 8.33 |
| WNT 2 | | 7.14 |
| WNT 5b | | 5.26 |
| LRP6 | 3.43 | |
| LRP3 | 2.27 | |
| LRP11 | | 10 |
| LRP12 | | 7.69 |
| DKK1 | | 50 |
| DKK3 | | 5.88 |
| FSZD5 | 4.48 | |
| FRZ9 | 3.85 | |
| FRZB | 3.36 | |
| FRZD1 | 2.94 | |
| SFRP2 | 2.95 | |
| FRZD1 | 2.92 | |
| FRZD3 | 2.84 | |
| AXIN2 | 4.4 | |
| KREMEN2 | 4.24 | |
| KREMEN1 | 3.45 | |
| b-CATENIN | | 4.76 |
| GSK3b | | 11.1 |
| GSK3a | | 6.67 |
| bFGF | | 50 |

Upon comparison, fibroblasts were found to regulate gene expression of bone morphogenetic protein (BMP) pathway genes in three-dimensional cultures within a hypoxic cultured naturally secreted ECM. Upregulation and downregulation of expression of various BMP pathway genes are evident in Table 5.

TABLE 5

Differential BMP Expression in Hypoxic
Three-Dimensional Fibroblast Cultures

| GENE | FOLD INCREASE | FOLD DECREASE |
|---|---|---|
| BMP7/OP1 | 4.88 | |
| BMP2 | 4.19 | |
| BMP5 | 3.49 | |
| BMP3 | 3.44 | |
| BMPrecIb | 3.37 | |
| BMP8b | 3.36 | |
| BMP 8a | 3.15 | |
| BMP 10 | 2.86 | |
| BMP1 | 2.12 | |
| BMPrecIa | | 2.5 |
| Osteocalcin | | 2.5 |
| Osteopontin | | 6.25 |
| BMPrecII | | 6.25 |

Upon comparison, fibroblasts were found to regulate expression of additional genes in three-dimensional cultures within a the hypoxic cultured naturally secreted ECM. Upregulation and downregulation of expression of additional genes are evident in Table 6.

TABLE 6

Additional Gene Expression Changes
Resulting from Low Oxygen Culture of Fibroblast ECM In Vivo.

| GENES | FOLD INCREASE | FOLD DECREASE |
|---|---|---|
| Collagens | | |
| COL5A1 | 6.21 | |
| COL9A2 | 3.96 | |
| COL6A2 | 3.78 | |
| COL6A2 | 3.21 | |
| COL11A1 | 3.07 | |
| COL8A1 | 2.78 | |
| COL4A5 | 2.45 | |
| COL7A1 | 2.45 | |
| COL18A1 | 2.41 | |
| COL12A1 | 2.04 | |
| COL1A2 | | 0.5 |
| COL14A1 | | 0.45 |
| COL4A1 | | 0.45 |
| COL5A2 | | 0.23 |
| COL6A1 | | 0.16 |
| Matrix Metalloproteinases (MMPs) | | |
| MMP23B | 2.75 | |
| MMP27 | | 0.24 |
| MMP28 | | 0.17 |
| MMP10 | | 0.16 |
| MMP1 | | 0.16 |
| MMP7 | | 0.1 |
| MMP14 | | 0.08 |
| MMP3 | | 0.06 |
| MMP12 | | 0.05 |
| Other ECM | | |
| HAPLN3 | 8.11 | |
| ACAN L12234 | 6.48 | |
| AGC1 | 3.32 | |
| LAMA3 | 2.92 | |
| LAMA1 | 2.14 | |
| LAMA5 | 2.14 | |

Example 2

Production of Hypoxic ECM Using Primary Human Neonatal Foreskin Fibroblasts

Two examples are provided for hypoxic culture of ECM using primary human neonatal foreskin fibroblasts.

Primary human neonatal foreskin fibroblasts were expanded in tissue culture flasks in the presence of 10% fetal bovine serum, 90% High Glucose DMEM with 2 mM L-glutamine (10% FBS/DMEM). Cells were subcultured using 0.05% trypsin/EDTA solution until the $3^{rd}$ passage at which time they were seeded to either Cytodex-1 dextran beads at 0.04 mgs dry beads/ml of medium ($5e^6$ cells/10 mgs beads in a 125 ml spinner flask filled with 100-120 mls), or to nylon mesh ($25e^6$ cells/6×100 $cm^2$ nylon). All cultures were kept in normal atmosphere and 5% $CO_2$ for expansion and seeding, at which point low oxygen cultures were split to an airtight chamber which was flooded with 95% nitrogen/5% $CO_2$ so that a hypoxic environment could be created within the culture medium. This system is maintains about 1-5% oxygen within the culture vessel. Cells were mixed well into the minimum volume needed to cover nylon or beads for seeding, and were subsequently mixed once after 30 minutes, then allowed to sit overnight in a humidified 37° C. incubator. Cultures were fed 10% FBS/DMEM for 2-4 weeks with a 50-70% media exchange, every 2-3 days while cells proliferated and then began depositing ECM. Cultures were fed for another 4-6 weeks using 10% bovine calf serum with iron supplement, and 20 ug/ml ascorbic acid in place of FBS. Spinner flasks were mixed at 15-25 rpm initially and for about 2-4 weeks, at which time they were increased to 45 rpm and maintained at this rate thereafter. Bead cultures formed large amorphous structures containing ECM of as much as 0.5 to 1.0 cm in width and diameter after 4 weeks, and these cultures were therefore hypoxic due to gas diffusion and high metabolic requirements.

In an additional example, primary human neonatal foreskin fibroblasts were expanded in monolayer flasks, and then cultured on nylon mesh scaffolds to support development of an extracellular matrix (ECM) in vitro. Fibroblasts were expanded in DMEM with high glucose, 2 mM L-glutamine, and 10% (v/v) fetal bovine serum. Cultures were also supplemented with 20 µg/ml ascorbic acid. After 3 weeks in ambient oxygen (approximately 16%-20% oxygen) duplicate ECM-containing cultures were switched to hypoxic culture conditions (1%-5% oxygen) in a sealed chamber flushed extensively with 95% nitrogen/5% carbon dioxide (Cat. # MC-101, Billups-Rothenberg, Inc., Del Mar, Calif.). To ensure depletion of atmospheric oxygen from the culture medium, 2-3 hours later the atmosphere was replaced to ensure that the medium contained approximately 1-3% oxygen. Both sets of ECM-containing cultures were grown with twice weekly feedings for another 4 weeks, and then cultures were prepared for RNA isolation. Total cellular RNA was isolated using a commercially available kit according to he manufacturers instructions (Cat. # Z3100, Promega, Inc.). Purified RNA samples were stored at −80° C., prior to processing for microarray analysis of gene expression using Agilent Whole Human Genome Oligo Microarrays®.

In analyzing the results, there were approximately 5,500 differentially expressed transcripts detected from probes prepared from ambient oxygen in comparison to probes from low oxygen cultures, using Agilent Whole Human Genome Oligo Microarrays®. Of these, about half (2,500) were greater than 2.0 fold increased by low oxygen, and about half (2,500) were decreased greater than 2.0 fold in low oxygen. This indicates that low oxygen led to significant changes in gene expression in vitro. Of particular interest, transcripts for ECM proteins, particularly a number of collagen genes were up-regulated, while a number of genes for matrix-degrading enzymes were down-regulated.

Example 3

Tissue-Engineered Human Embryonic Extracellular Matrix for Therapeutic Applications The embryonic extracellular matrix (ECM) creates an environment conducive to rapid cell proliferation and healing without the formation of scars or adhesions. It was hypothesized that the growth of human neonatal fibroblasts in 3 dimensions under conditions that simulate the early embryonic environment prior to angiogenesis (hypoxia and reduced gravitational forces) would generate an ECM with fetal properties. Gene chip array analysis showed the differential expression of over 5000 genes under the hypoxic versus traditional tissue culture conditions. The ECM produced was similar to fetal mesenchymal tissue in that it is relatively rich in collagens type III, IV, and V, and glycoproteins such as fibronectin, SPARC, thrombospondin, and hyaluronic acid. Since the ECM also plays an important regulatory role in binding and presenting growth factors in putative niches which support regenerative stem cell populations with key growth factors, we evaluated the effects of hypoxia on growth factor expression during the development of the fetal-like ECM in culture. Hypoxia can also enhance expression of factors which regulate wound healing and organogenesis, such as VEGF, FGF-7, and TGF-β, as well as multiple Wnt's including Wnt's 2b,4,7a,10a, and 11. The embryonic human ECM also stimulated an increase of metabolic activity in human fibroblasts in vitro, as measured by increased enzymatic activity using the MTT assay. Additionally, we detected an increase in cell number in response to human ECM. This human ECM can be used as a biological surface coating, and tissue filler treatment in various therapeutic applications where new tissue growth and healing without scarring or adhesions.

Example 4

Production of Naturally-Soluble WNT Activity for Regenerative Medicine Applications Stem or progenitor cells that can regenerate adult tissues, such as skin or blood, recapitulate embryonic development to some extent to accomplish this regeneration. A growing number of studies have shown that key regulators of stem cell pluripotency and lineage-specific differentiation active during embryogenesis are re-expressed in the adult under certain circumstances. The Wnt family of secreted morphogenetic growth and development factors is among the growth factors which can potentially provide valuable research tools and eventually therapeutic treatments in the clinic. However, Wnt's have proven refractory to standard recombinant expression and purification techniques to date on a commercial scale, and there are no reports of large-scale Wnt protein production to enable clinical development of Wnt-based products. Techniques have been developed for growing fetal-like ECM in culture using neonatal human dermal fibroblasts on various scaffolds in culture to generate three-dimensional tissue-equivalents. In this process, it was discovered that these cultures can provide a commercial-scale source of bioactive Wnt's contained in the serum-free conditioned medium used for ECM production. Here we present data on this Wnt product candidate.

Gene expression analysis of the cells demonstrated that at least 3 WNT genes were expressed (Wnt 5a, Wnt 7a, and Wnt 11), and a small number of genes related to Wnt signaling were expressed as well; however, their function is not completely understood. The gene expression data was extended to an in vitro bioassay for Wnt-signaling (nuclear translocation of β-catenin in primary human epidermal keratinocytes) and Wnt activity on blood stem cells was evaluated. Both assays demonstrated activity consistent with canonical Wnt activity. Furthermore, conditioned media from these cultures showed Wnt activity when injected into the skin of mice, inducing hair follicle stem cells to enter anagen, thus causing hair growth. This indicates that the stabilized Wnt activity within the defined and serum-free condition medium did not require purification. This product can be used for hair follicle regeneration and as a valuable research tool for the culture of various human stem cells.

Example 5

Hypoxic Fibroblasts Demonstrate Unique ECM Production and Growth Factor Expression Human neonatal dermal fibroblasts produce an ECM when cultured in vitro, which closely mimics the dermis and which can replace the damaged dermis in regenerative medicine applications such as wound healing. Since the process of wound healing also recapitulates embryonic development, by simulating the embryonic environment we hypothesize that the ECM produced will provide an enhanced ECM for tissue regeneration applications. Therefore, human neonatal fibroblast-derived ECM were grown under hypoxic conditions in culture, to simulate the hypoxia which exists in the early embryo prior to angiogenesis. The goal was to generate an ECM with fetal properties using hypoxic conditions during tissue development in culture.

The ECM produced in these hypoxic cultures was similar to fetal mesenchymal tissue in that it is relatively rich in collagens type III and V, and glycoproteins such as fibronectin, SPARC, thrombospondin, and hyaluronic acid. Since the ECM also plays an important regulatory role in binding and presenting growth factors in putative niches which support regenerative stem cell populations with key growth factors, we evaluated the effects of hypoxia on growth factor expression during the development of the fetal-like ECM in culture. It was shown that hypoxia can also enhance expression of factors which regulate wound healing and organogenesis, such as VEGF, FGF-7, and TGF-β.

The human ECM also stimulated an increase of metabolic activity in human fibroblasts in vitro, as measured by increased enzymatic activity using the MTT assay. Additionally, an increase in cell number in response to human ECM was detected. These results support the use of this human ECM as a coating/scaffold in embryonic cell cultures and as a biological surface coating/filler in various therapeutic applications or medical devices.

Example 6

Extracellular Matrix Compositions in Melanoma, Glioma, and Breast Cancer

Tumor growth of B16 (melanoma cell line), C6 (glioma cell line), and MDA 435 (breast cancer cell line) cells, in the presence or absence of ECM, and with or without cisplatin, were examined in a chorioallantoic membrane of the fertilized chicken egg assay (CAM). Briefly, eggs were candled for viability. The air sack was displaced creating a blister between the shell and chorioallantoic membranes at the equator of the egg. A window was cut through the shell to gain access to the CAM. Cells were added to the CAM as follows: B16 cells, 5 million per egg; C6 cells, 5 million per egg; and MD435 cells, 5 million per egg. In the eggs treated with ECM, the ECM (~100 μg/treatment) and cells were added to the eggs at the same time. In the eggs treated with cisplatin, the cisplatin (250 μL of 1 mg/mL cisplatin solution) was added topically the next day. The eggs were incubated for 10 days at which time the tumors were removed and weighed.

Figure 2:
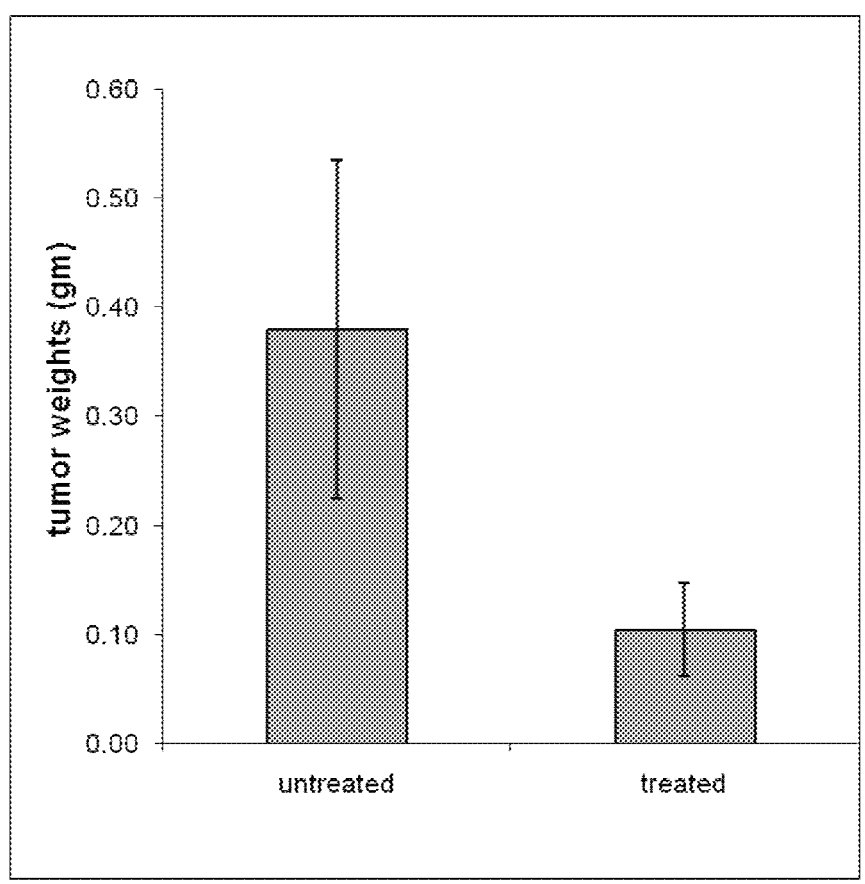
FIG. 2 shows a plot of tumor weight of B16 cells in the presence and absence of ECM in the CAM assay.
Figure 3:
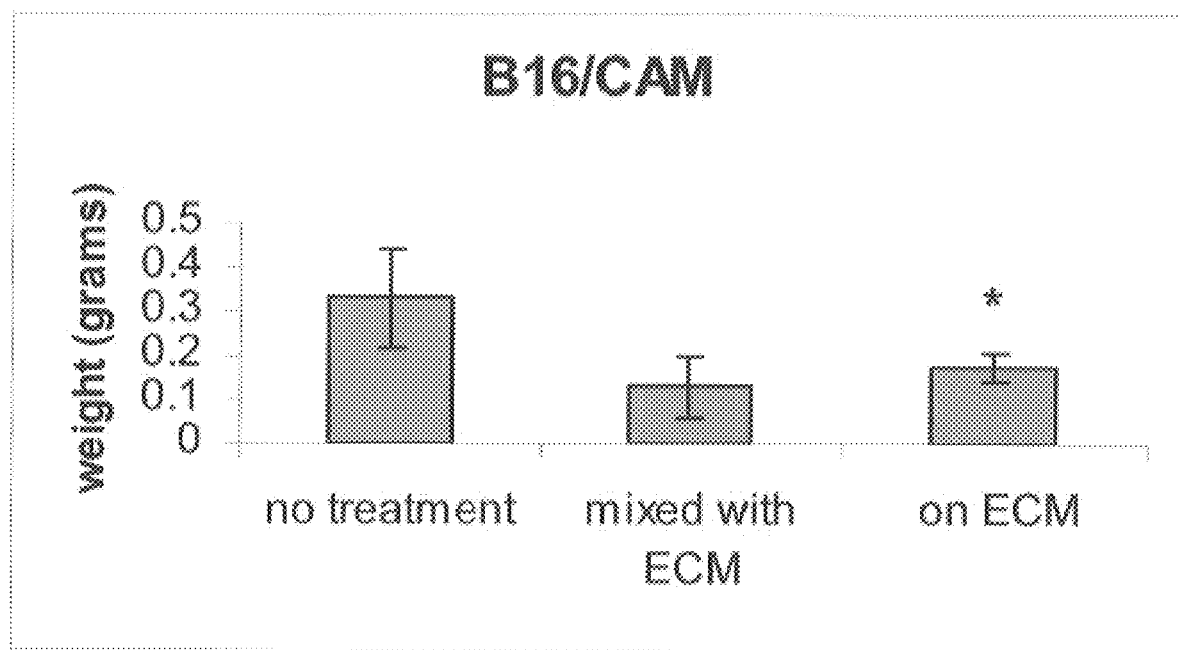
FIG. 3 shows a plot of tumor weight of B1 cells grown in the absence of ECM, mixed with ECM, or on ECM in the CAM assay.
Figure 4:
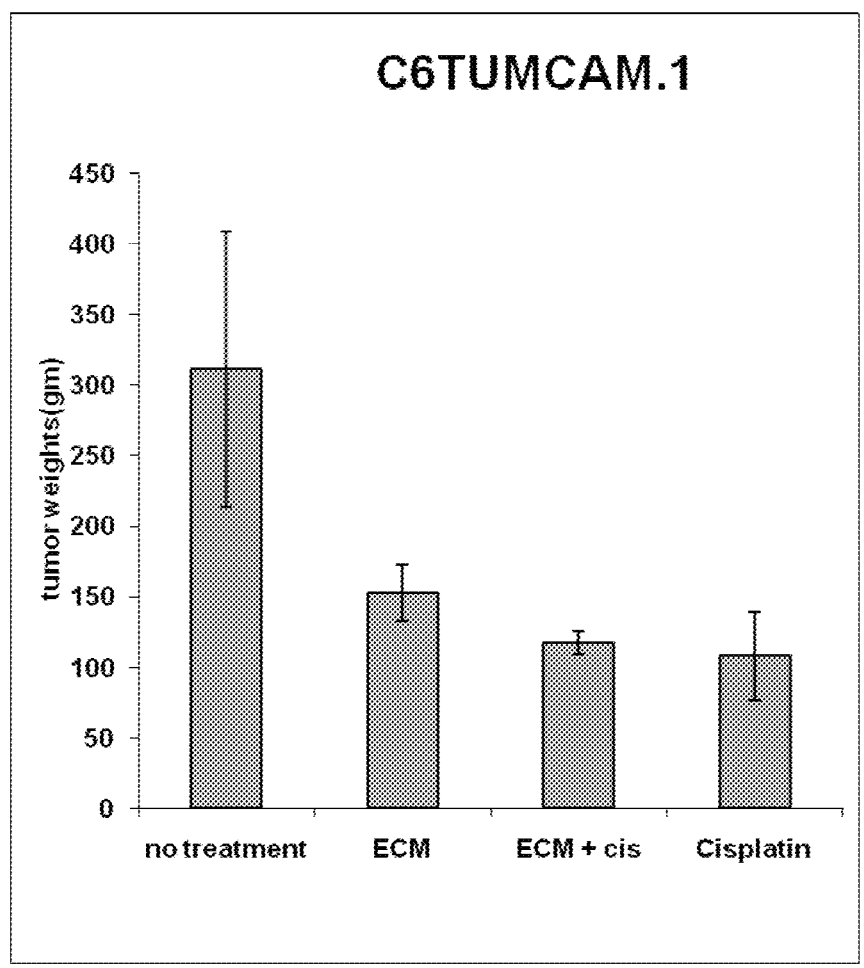
FIG. 4 shows a plot of tumor weight of C6 cells in the presence and absence of ECM, with or without cisplatin in the CAM assay.
Figure 5:
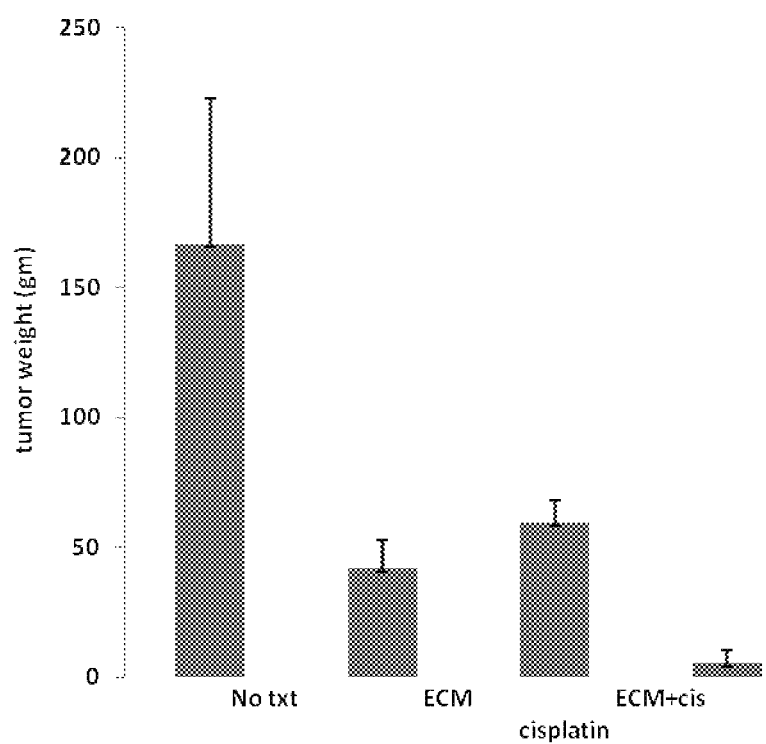
FIG. 5 shows a plot of tumor weight of C6 cells in the presence and absence of ECM, with or without cisplatin in the CAM assay.
Figure 6A:
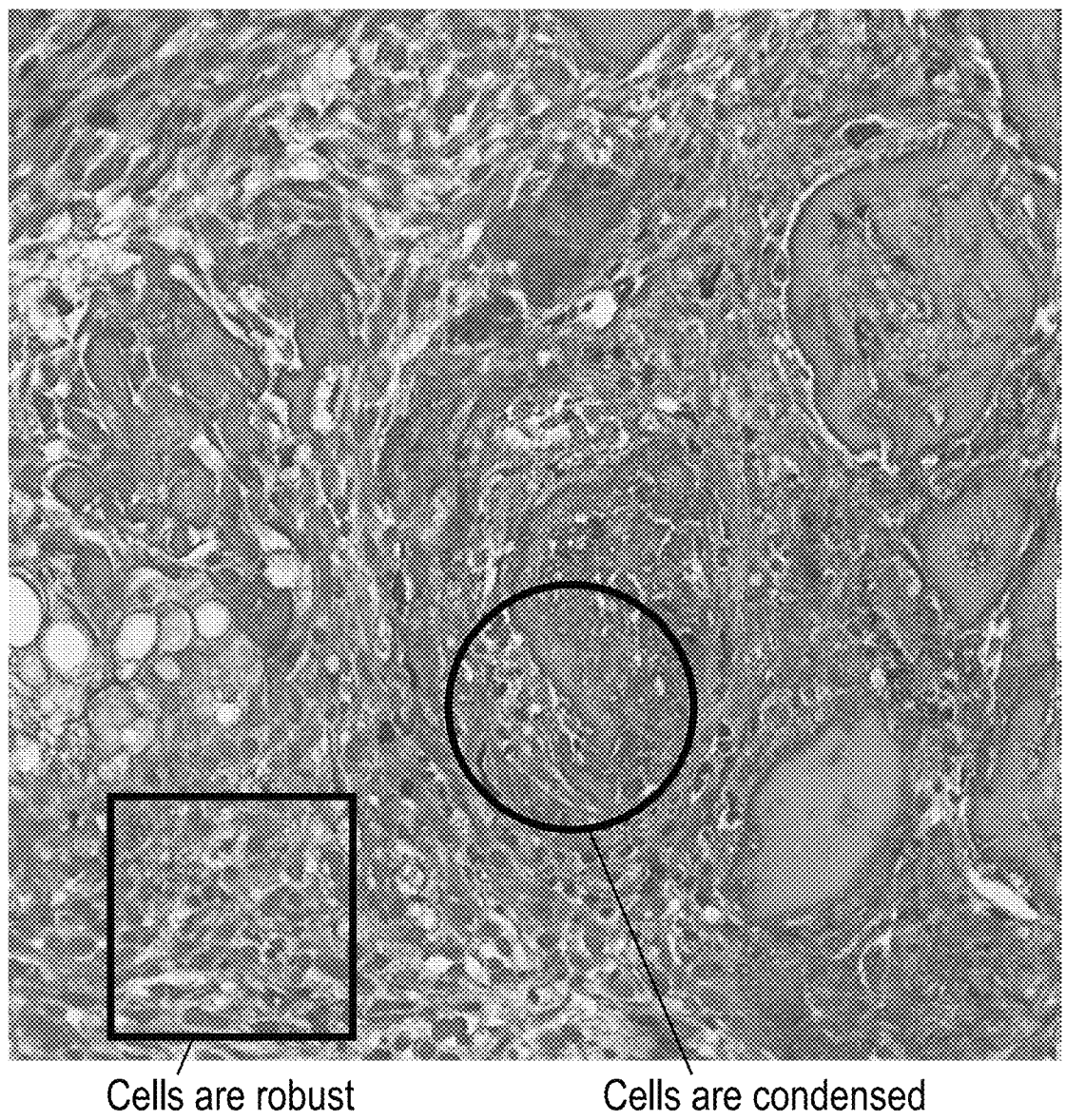
FIGS. 6A and 6B show photographs of histologic analysis of C6 glioma tumors grown in the presence or absence of ECM.
Figure 6B:
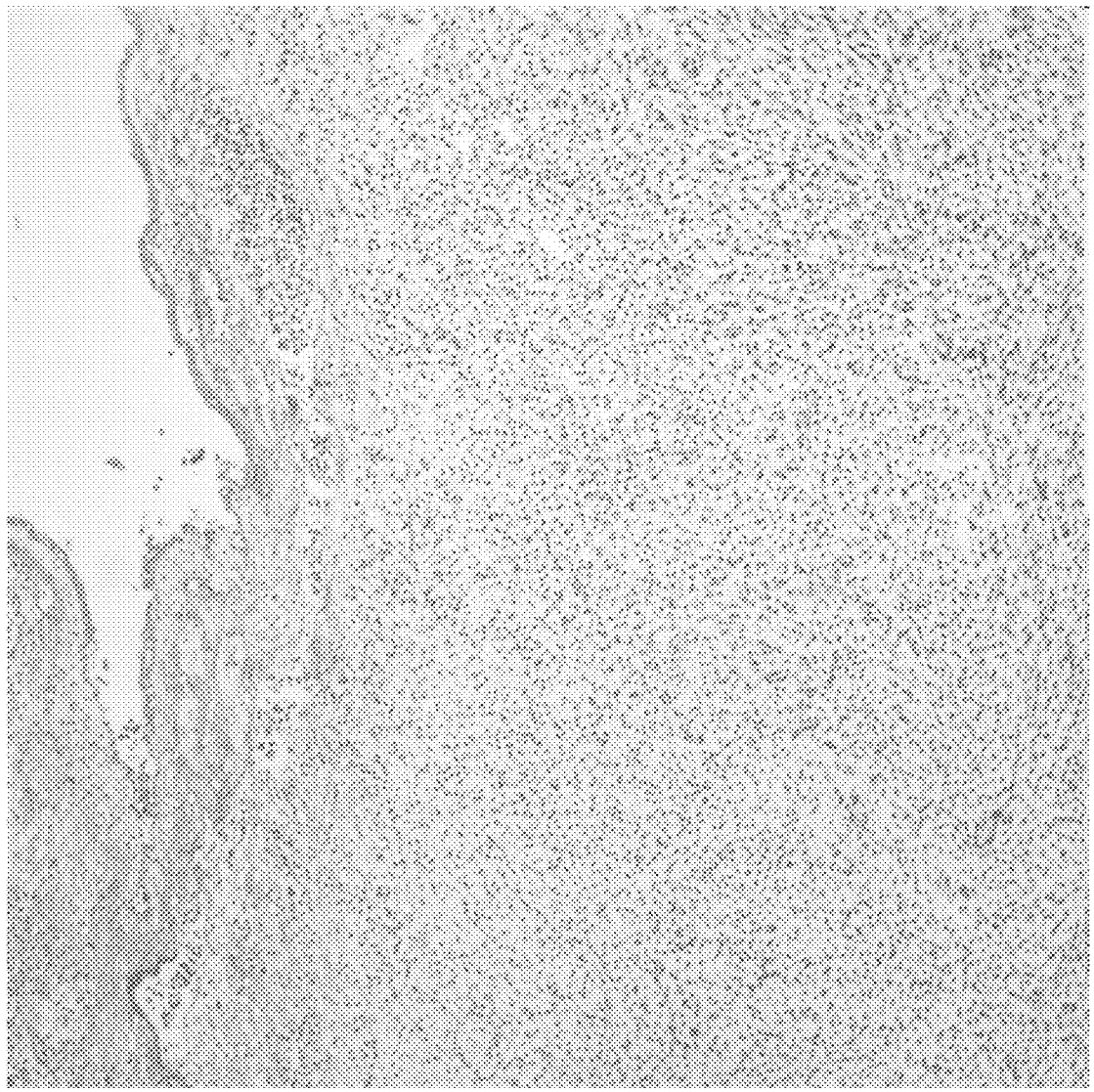
Figure 7:
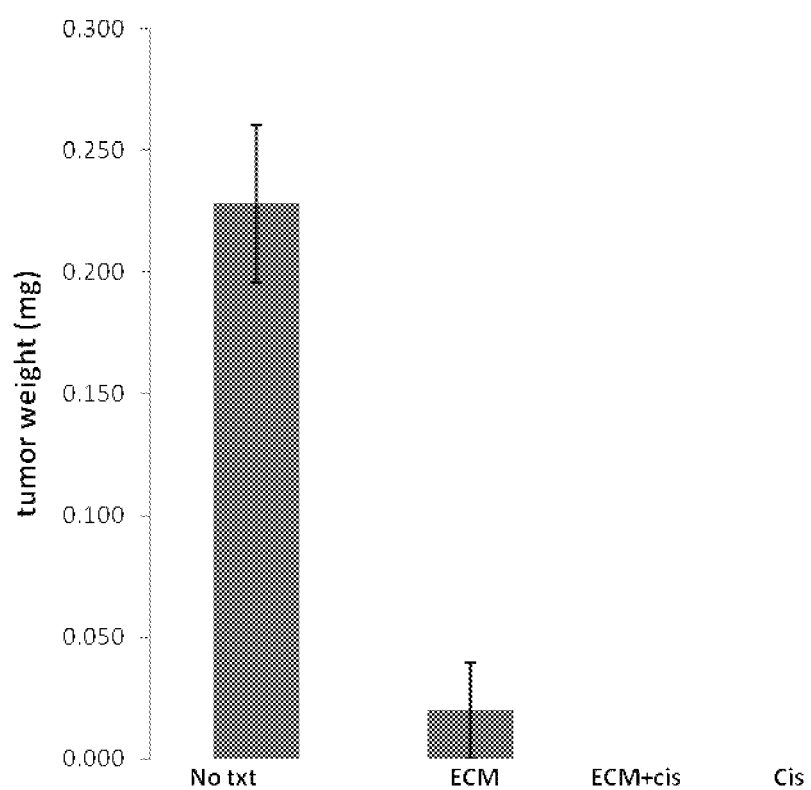
FIG. 7 shows a plot of tumor weight of MDA 435 cells grown in the presence and absence of ECM in the CAM assay.

Tumor mass was significantly reduced by the presence of ECM. FIGS. 1 and 2 show that the weight of tumors produced by B16 cells was reduced in the presence of ECM versus the absence of ECM. The weight of tumors was also reduced whether tumor cells were mixed with ECM or grown on ECM (FIG. 3). FIGS. 4 and 5 show that the weight of tumors produced by C6 cells was reduced in the presence of ECM versus no treatment. Moreover, tumor weight was further reduced in the presence of ECM with cisplatin. FIG. 7 shows that the weight of tumors produced by MDA 435 breast cancer cells was reduced in the presence of ECM versus no treatment and was further reduced by ECM with cisplatin.

Figure 16:
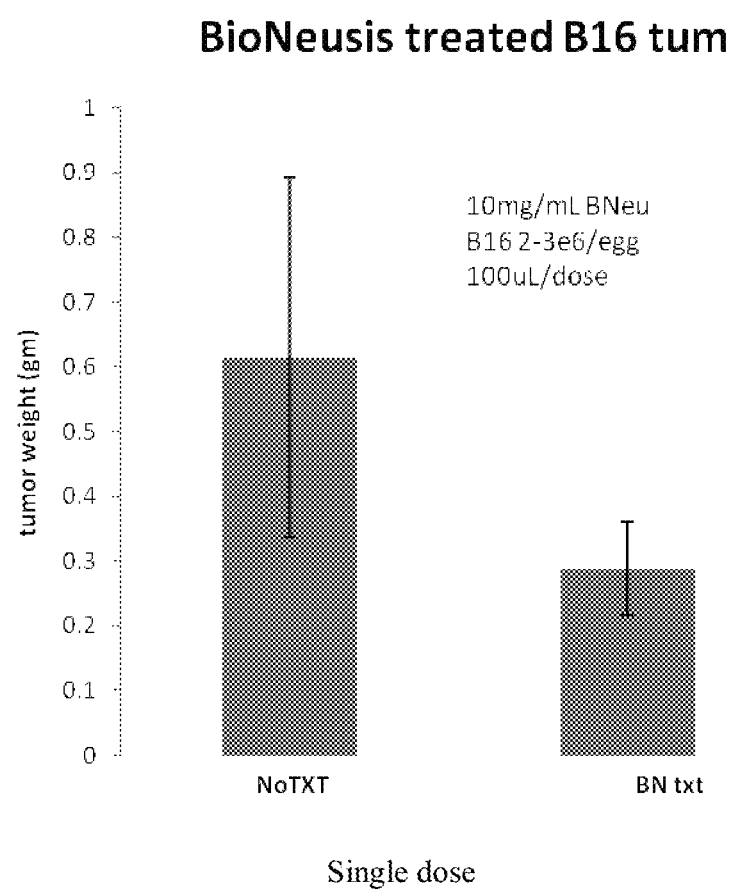
FIG. 16 shows a plot of tumor weight of B16 cells in the presence and absence of liquid ECM in the CAM assay.
Figure 17:
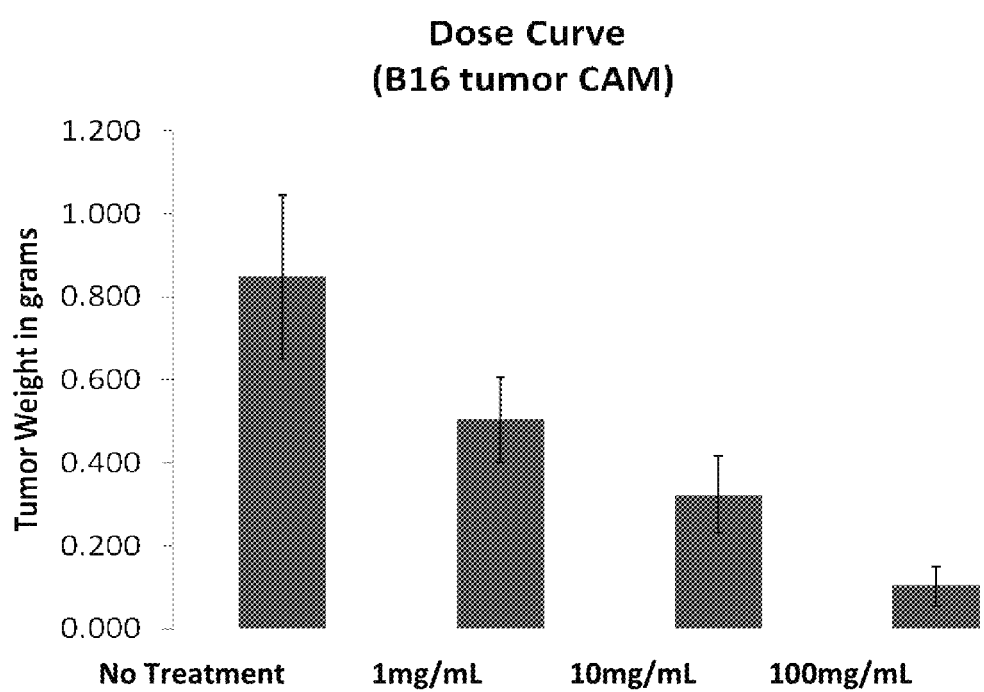
FIG. 17 shows a dose response curve of tumor weight of B16 cells grown in the presence of liquid ECM in the CAM assay.
Figure 18:
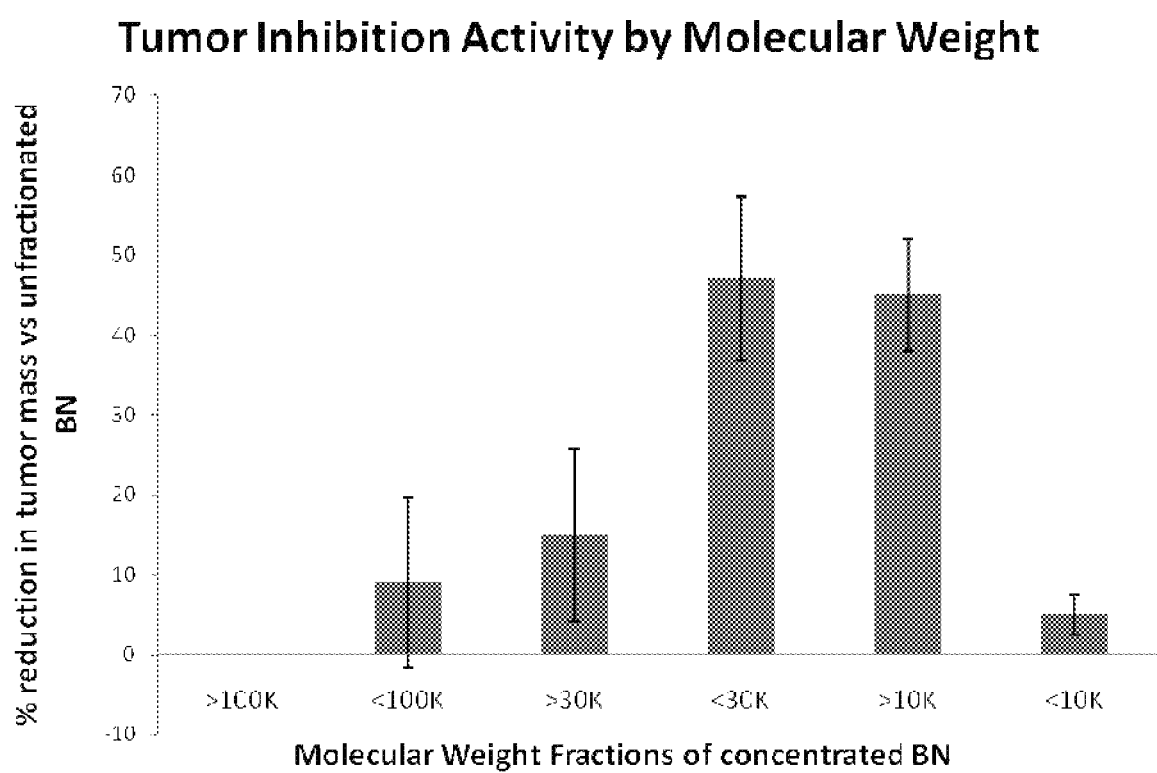
FIG. 18 shows a plot of tumor weight of B16 cells grown in liquid ECM of various molecular weight fractions in the CAM assay.

In another CAM assay, B16 cells were injected into eggs (2-3 million cells/egg) with a 100 μL dose of BioNeusis (10 mg/mL). BioNeusis is the medium conditioned by the fibroblasts in the bioreactor used to generate ECM and is very similar to the ECM only in liquid form. FIG. 16 shows the tumor growth in the CAM assay was reduced in the presence of BioNeusis as compared to no treatment. In a further study, B16 cells were grown in the presence of increasing concentrations of liquid ECM, with growth reduced in all concentrations of ECM (FIG. 17). In another study, B16 cells were grown in liquid ECM of various molecular weight fractions as compared to B16 cells grown in unfractionated liquid ECM in the CAM assay. All molecular weight fractions except the >100,000 dalton fraction showed an increase in the percent reduction of tumor mass as compared to unfractionated ECM (FIG. 18).

Figure 8:
FIG. 8 shows a photograph of tumor growth of C6 cells with no treatment in nude mice.
Figure 9:
FIG. 9 shows a photograph of tumor growth of C6 cells with hECM treatment in nude mice.
Figure 10:
FIG. 10 shows a photograph of tumor growth of C6 cells with ECM plus cisplatin treatment in nude mice.
Figure 11:
FIG. 11 shows a photograph of tumor growth of C6 cells with cisplatin treatment in nude mice.
Figure 12:
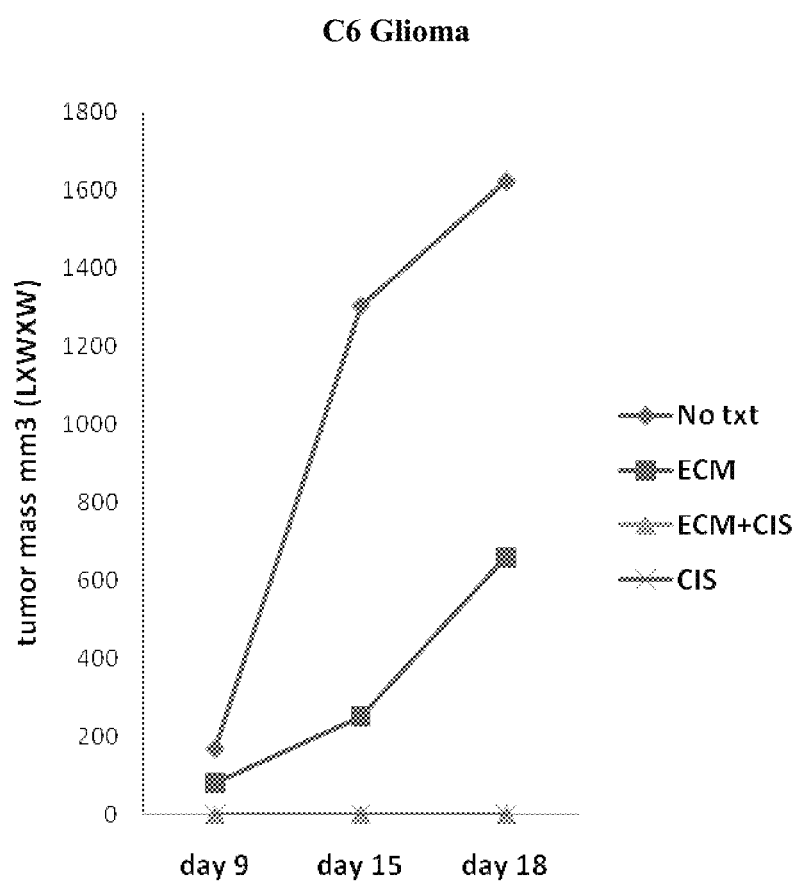
FIG. 12 shows a plot of the growth of C6 glioma tumors in nude mice in the presence or absence of ECM, with or without cisplatin.
Figure 13A:
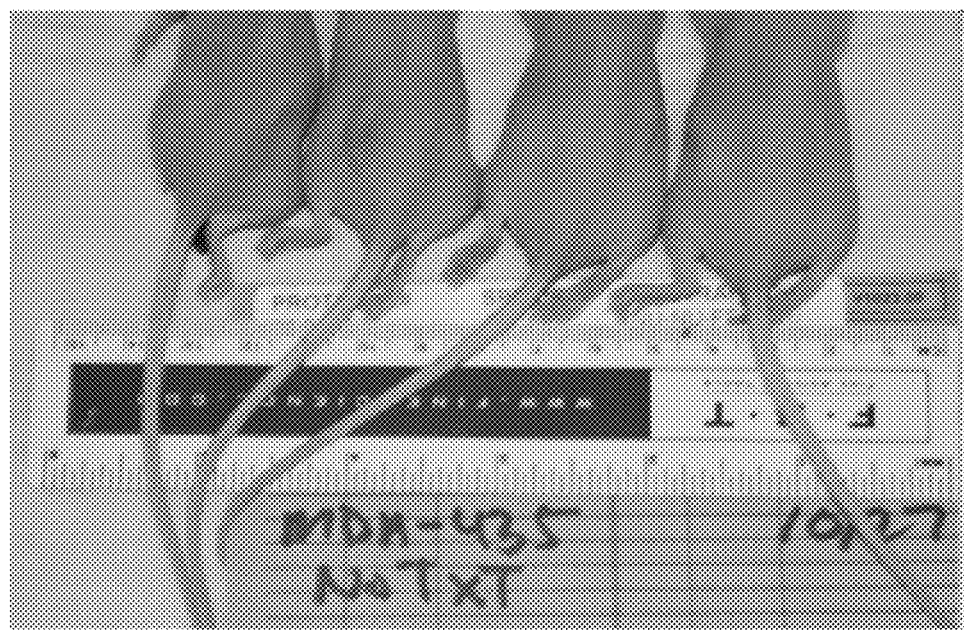
FIGS. 13A-D show photographs of tumor growth of MDA 435 cells in nude mice with no treatment (FIG. 13A), hECM treatment (FIG. 13B), hECM plus cisplatin treatment (FIG. 13C) and hECM with cisplatin treatment (FIG. 13D).
Figure 13B:
Figure 13C:
Figure 13D:
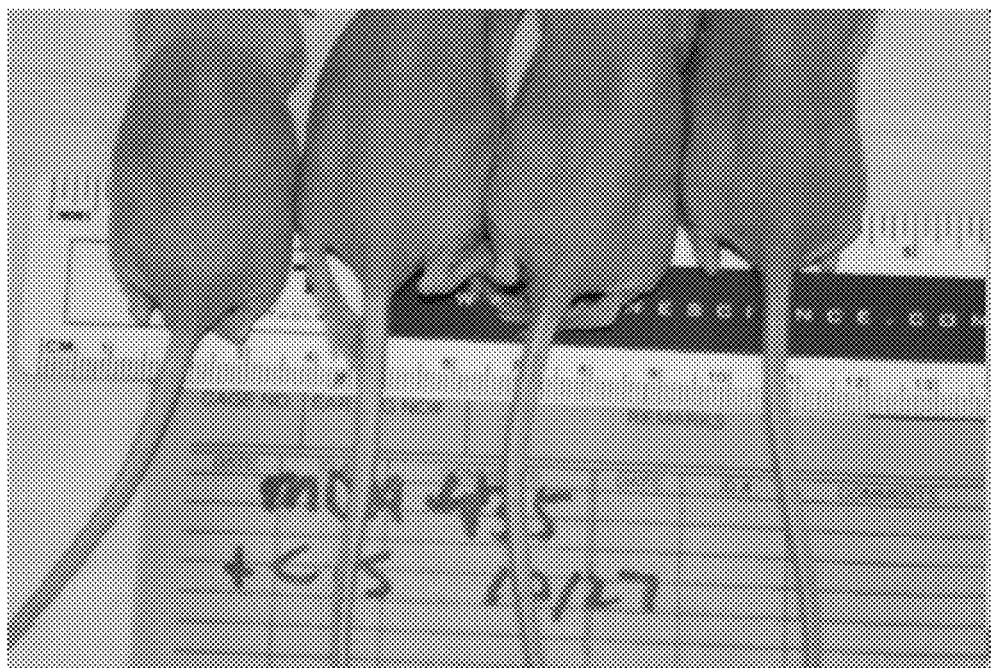
Figure 14:
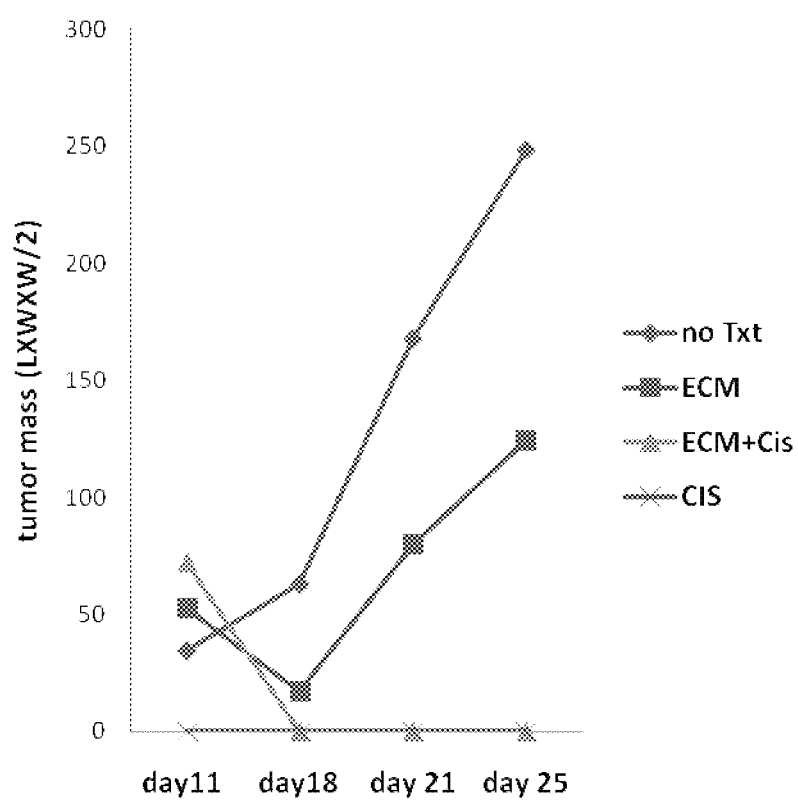
FIG. 14 shows a plot of the growth of MDA 435 tumors in nude mice in the presence or absence of ECM, with or without cisplatin.
Figure 15:
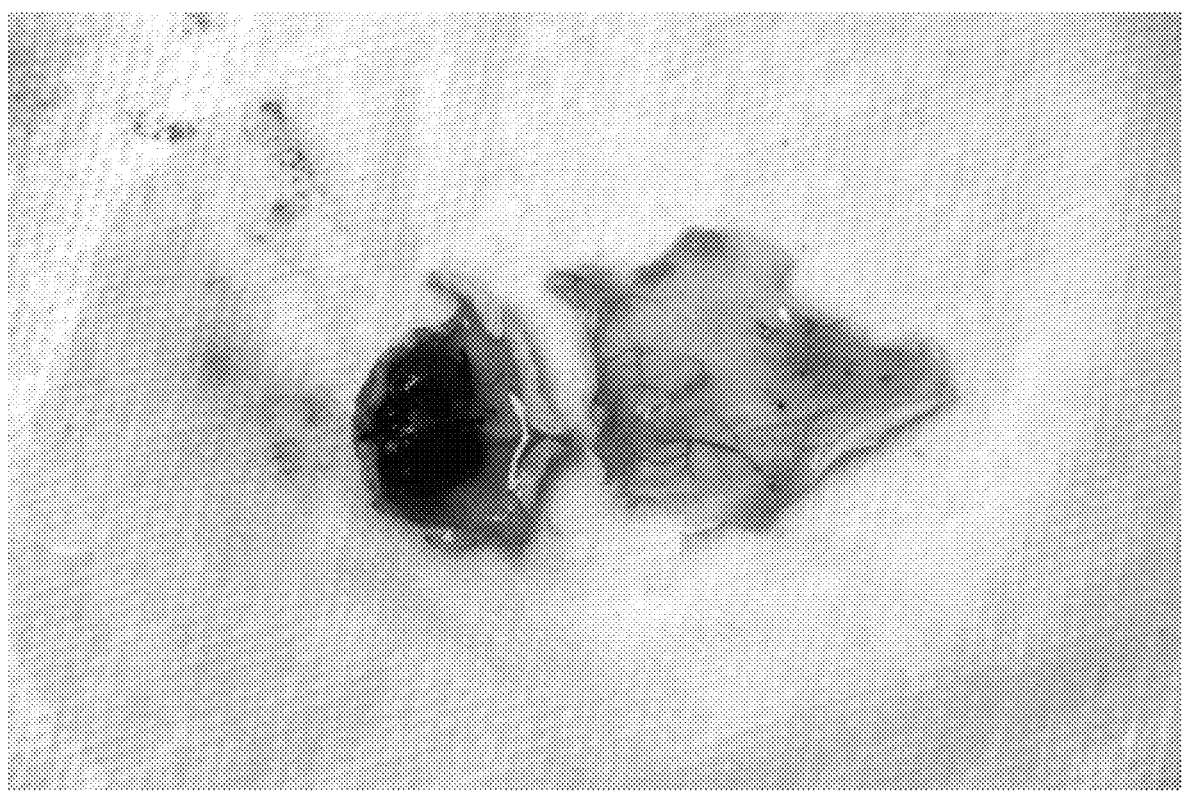
FIG. 15 shows a photograph of tumor growth of B16 cells with (specimen on right) and without ECM (specimen on left) in rodents.

Tumor growth of B16 cells, C6 cells, or MDA435 cells in the presence or absence of ECM, and with or without cisplatin, were examined in nude mice. Cells, ECM and Cisplatin were injected simultaneously subcutaneously in the lower haunch of a nude mouse. Tumor growth was followed over time using photography, measurements of length and width, then finally by weight. FIGS. 8 and 9 show the growth of tumors from C6 cells in nude mice in the presence (FIG. 9) and absence (FIG. 8) of ECM on day 14 post-injection. FIGS. 10 and 11 show the growth of tumors from C6 cells in nude mice in the presence of ECM with cisplatin (FIG. 10) and cisplatin without ECM (FIG. 11) of ECM on day 14 post-injection. Cells grown with ECM showed reduced or no tumor growth, in comparison to the control (no treatment) which did form palpable tumors. FIG. 12 shows a plot of the tumor growth over 18 days in which mice treated with ECM showed reduced tumor growth, as compared to the no treatment control and mice treated with cisplatin, with or without ECM showed no growth. In an analogous study, MDA435 cells grown with ECM (FIG. 13B), with ECM plus cisplatin (FIG. 13C), or with cisplatin alone (FIG. 13D) showed reduced or no tumor growth, in comparison to the no treatment control (FIG. 13A), which did form palpable tumors. FIG. 14 shows a plot of the tumor growth over 25 days in which mice treated with ECM showed reduced tumor growth, as compared to the no treatment control. Mice treated with cisplatin, with or without ECM showed a reduction in tumor mass to zero. FIG. 15 shows the results of B16 cells grown in nude mice with ECM (right side) or without (left side) ECM, in which tumor growth was inhibited in the presence of ECM.

Example 7

Inhibition of Metastasis of Adenocarcinoma Using Extracellular Matrix Compositions Metastasis of primary tumors of HCT cells (human colon adenocarcinoma cell line), in the presence and absence of ECM (both insoluble (iECM) and soluble (sECM) fractions), were examined in a chorioallantoic membrane of the fertilized chicken egg assay (CAM). Briefly, eggs were processed as previously described. Tumors were formed by subsequent exposure to HCT cells and incubation. Samples were stained with fluorescently labeled anti-CD44+ antibodies (green) and examined by fluorescence microscopy. In the control sample (no ECM treatment), high numbers of cancer cells were observed migrating out of the metastasizing primary tumor mass and entering circulation. In samples treated with either iECM or sECM, metastasis was greatly inhibited as few or no cancer cells were observed migrating out of primary tumor masses.

Although the invention has been described with reference to the above examples and Attachment 1, the entire contents of which are incorporated herein by reference, it will be understood that modifications and variations are encompassed within the spirit and scope of the invention. Accordingly, the invention is limited only by the following claims.

What is claimed is:

1. A method of treating cancer in a subject comprising administering an ECM to the subject wherein the ECM is produced by the method comprising culturing fibroblast cells on microbeads under hypoxic conditions of 1-5% oxygen to produce a hypoxic ECM composition, thereby treating the cancer.

2. The method of claim 1, wherein the cancer is selected from the group consisting of melanoma, glioma, adenocarcinoma, bladder cancer, bone cancer, cancer of the bone marrow, brain cancer, spinal cancer, breast cancer, cervical cancer, gall bladder cancer, cancer of the ganglia, cancer of the gastrointestinal tract, stomach cancer, colon cancer, cancer of the heart, kidney cancer, liver cancer, lung cancer, muscle cancer, ovarian cancer, pancreatic cancer, parathyroid cancer, cancer of the penis, prostate cancer, cancer of the salivary glands, skin cancer, cancer of the spleen, cancer of the testis, thymus cancer, thyroid cancer, and uterine cancer.

3. The method of claim 1, wherein the hypoxic ECM composition has a soluble fraction.

4. The method of claim 1, wherein the hypoxic ECM composition has a non-soluble fraction.

5. The method of claim 1, wherein the hypoxic ECM composition is a combination of a soluble and non-soluble fraction.

6. The method of claim 3, wherein the soluble fraction comprises a molecular weight fraction comprising molecules having a molecular weight less than 30,000 Daltons.

7. The method of claim 6, wherein the molecules have a molecular weight less than 5,000 Daltons.

8. The method of claim 1, further comprising administrating to the subject an anti-inflammatory agent, antihistamines, chemotherapeutic agent, immunomodulator, therapeutic antibody or a protein kinase inhibitor.

9. The method of claim 8, wherein the chemotherapeutic agent is an alkaloid; covalent DNA-binding agent; noncovalent DNA-binding agent; antimetabolite; enzyme; hormone; platinum compound; monoclonal antibody conjugated with anticancer a drug, toxin, and/or radionucleotide; biological response modifier; hematopoietic growth factor; inhibitor of angiogenesis; DNA cross-linking agent; topoisomerase I inhibitor; or microtubule inhibitor.

10. The method of claim 8, wherein the chemotherapeutic agent is selected from the group consisting of 2-Chlorodeoxyadenosine, 2'-Deoxycoformycin, 2'-Deoxycoformycin, 5-fluorouracil, 5-fluorodeoxyuridine, 4-dimethoxy-daunomycin, 11-deoxydaunorubicin, 13-deoxydaunorubicin, adriamycin-14-benzoate, adriamycin-14-octanoate, adriamycin-14-naphthaleneacetate, 6-Mercaptopurine, 6-Thioguanine, acyclovir, amsacrine, anastrozole, asparaginase, azathioprine, busulfan, camptothecin, canbusil, carboplatin, carminomycin, carmustine, chlorambucil, chlorodeoxyadenosine, cisplatin, cyclophosphamide, cytarabine, dactinomycin, dacarbazine, daunorubicin, doxorubicin, docetaxel, doxorubicin, epirubicin, etoposide, fludarabine, flutamide, hydroxymethylmelamine, idarubicin, ifosphamide, isirinotecan, lomustine, lovastatin, mechlorethamine, melphalan, methotrexate, mithoxanthrone, mitocycin, oxalaplatin, semustine, thiotepa, tamoxifen, taxol, taxotere; teniposide, thioguanine, topetecan, vincristine, vinblastine, and vindesine.

11. The method of claim 1, wherein the subject had a previous surgical resection.

12. The method of claim 1, wherein the hypoxic ECM further comprises a chemotherapeutic agent and/or an immunomodulatory agent.

13. The method of claim 12, wherein the chemotherapeutic agent is selected from the group consisting of 2-Chlorodeoxyadenosine, 2'-Deoxycoformycin, 2'-Deoxycoformycin, 5-fluorouracil, 5-fluorodeoxyuridine, 4-dimethoxy-daunomycin, 11-deoxydaunorubicin, 13-deoxydaunorubicin, adriamycin-14-benzoate, adriamycin-14-octanoate, adriamycin-14-naphthaleneacetate, 6-Mercaptopurine, 6-Thioguanine, azathioprine, acyclovir, amsacrine, anastrozole, asparaginase, busulfan, camptothecin, canbusil, carboplatin, carminomycin, carmustine, chlorambucil, chlorodeoxyadenosine, cisplatin, cyclophosphamide, cytarabine, dactinomycin, dacarbazine, daunorubicin, doxorubicin, docetaxel, doxorubicin, epirubicin, etoposide, fludarabine, flutamide, hydroxymethylmelamine, idarubicin, ifosphamide, isirinotecan, lomustine, lovastatin, mechlorethamine, melphalan, methotrexate, mithoxanthrone, mitocycin, oxalaplatin, semustine, thiotepa, tamoxifen, taxol, taxotere; teniposide, thioguanine, topetecan, vincristine, vinblastine, and vindesine.

14. The method of claim 1, wherein the fibroblast cells are human.

15. The method of claim 1, wherein the fibroblast cells are adult, fetal, neonatal or embryonic fibroblast cells.

* * * * *